US009307895B2

(12) United States Patent
Adair et al.

(10) Patent No.: US 9,307,895 B2
(45) Date of Patent: *Apr. 12, 2016

(54) REDUCED AREA IMAGING DEVICE INCORPORATED WITHIN ENDOSCOPIC DEVICES

(71) Applicants: Jeffrey L. Adair, Highlands Ranch, CO (US); Kevin Ewing Wiggins, Denver, CO (US)

(72) Inventors: Jeffrey L. Adair, Highlands Ranch, CO (US); Kevin Ewing Wiggins, Denver, CO (US)

(73) Assignee: MICRO-IMAGING SOLUTIONS, LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/291,583

(22) Filed: May 30, 2014

(65) Prior Publication Data

US 2014/0364689 A1   Dec. 11, 2014

Related U.S. Application Data

(63) Continuation of application No. 13/732,908, filed on Jan. 2, 2013, now Pat. No. 8,885,034, which is a continuation of application No. 12/889,287, filed on Sep. 23, 2010, now abandoned, which is a (Continued)

(51) Int. Cl.
*A61B 1/04* (2006.01)
*A61B 1/05* (2006.01)
(Continued)

(52) U.S. Cl.
CPC . *A61B 1/05* (2013.01); *A61B 1/008* (2013.01); *A61B 1/00009* (2013.01);
(Continued)

(58) Field of Classification Search
USPC .............................. 348/76; 600/110
See application file for complete search history.

(56) References Cited

U.S. PATENT DOCUMENTS 4,164,182 A   8/1979   Sato
4,491,865 A   1/1985   Danna et al.
(Continued)

FOREIGN PATENT DOCUMENTS

AT   320693   4/2006
AU   7004101   1/2002
(Continued)

OTHER PUBLICATIONS

"Camera phone technology," eWebsite.com, 1997, 3 pages.
(Continued)

*Primary Examiner* — Geepy Pe
*Assistant Examiner* — Asmamaw G. Tarko
(74) *Attorney, Agent, or Firm* — Sheridan Ross P.C.

(57) ABSTRACT

A reduced area imaging device is provided for use in medical or dental instruments such as an endoscope. The imaging device is provided in various configurations, and connections between the imaging device elements and a video display may be achieved by wired or wireless connections. A connector assembly located near the imaging device interconnects the imaging device to an image/power cable extending through the endoscope. The connector provides strain relief and stabilization for electrically interconnecting the imager to the cable. The connector also serves as the structure for anchoring the distal ends of steering wires extending through the body of the endoscopic device. The connector includes a strain relief member mounted over a body of the connector. The connector allows a steering wire capability without enlarging the profile of the distal tip of the endoscopic device.

8 Claims, 17 Drawing Sheets

Related U.S. Application Data continuation-in-part of application No. 11/245,960, filed on Oct. 6, 2005, which is a continuation of application No. 09/929,531, filed on Aug. 13, 2001, now Pat. No. 7,030,904, which is a continuation-in-part of application No. 09/496,312, filed on Feb. 1, 2000, now Pat. No. 6,275,255, which is a continuation of application No. 09/175,685, filed on Oct. 20, 1998, now Pat. No. 6,043,839, which is a continuation-in-part of application No. 08/944,322, filed on Oct. 6, 1997, now Pat. No. 5,929,901.

(51) Int. Cl.

| | |
|---|---|
| *A61B 1/00* | (2006.01) |
| *A61B 1/055* | (2006.01) |
| *A61B 1/06* | (2006.01) |
| *H04N 5/232* | (2006.01) |
| *H04N 5/374* | (2011.01) |
| *A61B 1/008* | (2006.01) |
| *A61B 1/045* | (2006.01) |
| *H04N 5/3745* | (2011.01) |
| *A61B 1/002* | (2006.01) |
| *H04N 5/225* | (2006.01) |

(52) U.S. Cl.
CPC ........ *A61B 1/00016* (2013.01); *A61B 1/00045* (2013.01); *A61B 1/00064* (2013.01); *A61B 1/042* (2013.01); *A61B 1/045* (2013.01); *A61B 1/051* (2013.01); *A61B 1/055* (2013.01); *A61B 1/0607* (2013.01); *H04N 5/23203* (2013.01); *H04N 5/374* (2013.01); *H04N 5/3745* (2013.01); *A61B 1/002* (2013.01); *H04N 2005/2255* (2013.01)

(56) References Cited

U.S. PATENT DOCUMENTS

| | | | |
|---|---|---|---|
| 4,573,450 A | 3/1986 | Arakawa | |
| 4,706,654 A | 11/1987 | Ogiu et al. | |
| 4,745,471 A | 5/1988 | Takamura et al. | |
| 4,786,965 A | 11/1988 | Yabe | |
| 4,814,648 A | 3/1989 | Hynecek | |
| 4,854,302 A | 8/1989 | Allred, III | |
| 4,869,246 A | 9/1989 | Adair | |
| 4,928,300 A | 5/1990 | Ogawa et al. | |
| 4,942,473 A | 7/1990 | Zeevi et al. | |
| 5,021,888 A | 6/1991 | Kondou et al. | |
| RE33,854 E | 3/1992 | Adair | |
| 5,116,317 A | 5/1992 | Carson, Jr. et al. | |
| 5,162,913 A | 11/1992 | Chatenever et al. | |
| 5,191,601 A | 3/1993 | Ida et al. | |
| 5,220,198 A | 6/1993 | Tsuji | |
| 5,251,613 A | 10/1993 | Adair | |
| 5,381,784 A | 1/1995 | Adair | |
| 5,402,768 A | 4/1995 | Adair | |
| 5,453,785 A | 9/1995 | Lenhardt et al. | |
| 5,471,515 A | 11/1995 | Fossum et al. | |
| 5,489,256 A | 2/1996 | Adair | |
| 5,495,114 A | 2/1996 | Adair | |
| 5,603,697 A * | 2/1997 | Grundy ................. | A61B 18/18 604/95.04 |
| 5,605,531 A | 2/1997 | Lane et al. | |
| 5,612,732 A | 3/1997 | Yuyama et al. | |
| 5,630,782 A | 5/1997 | Adair | |
| 5,630,783 A | 5/1997 | Steinberg | |
| 5,682,199 A | 10/1997 | Lankford | |
| 5,701,155 A | 12/1997 | Wood et al. | |
| 5,711,013 A | 1/1998 | Collett et al. | |
| 5,734,418 A | 3/1998 | Danna | |
| 5,748,411 A | 5/1998 | Hwang | |
| 5,748,441 A | 5/1998 | Loritz et al. | |
| 5,754,313 A | 5/1998 | Pelchy et al. | |
| 5,801,919 A | 9/1998 | Griencewic | |
| 5,817,015 A | 10/1998 | Adair | |
| 5,840,013 A | 11/1998 | Lee et al. | |
| 5,873,814 A | 2/1999 | Adair | |
| 5,879,289 A | 3/1999 | Yarush et al. | |
| 5,900,875 A | 5/1999 | Haitani et al. | |
| 5,913,816 A | 6/1999 | Sanders et al. | |
| 5,929,901 A | 7/1999 | Adair et al. | |
| 5,980,450 A | 11/1999 | Thompson | |
| 5,983,073 A | 11/1999 | Ditzik | |
| 5,986,693 A | 11/1999 | Adair et al. | |
| 6,002,437 A | 12/1999 | Morioka et al. | |
| 6,009,336 A | 12/1999 | Harris et al. | |
| 6,018,670 A | 1/2000 | Degenhardt | |
| 6,023,241 A | 2/2000 | Clapper | |
| 6,028,764 A | 2/2000 | Richardson et al. | |
| 6,037,034 A | 3/2000 | Asseier et al. | |
| 6,043,839 A | 3/2000 | Adair et al. | |
| 6,067,313 A | 5/2000 | Cafarella et al. | |
| 6,073,034 A | 6/2000 | Jacobsen et al. | |
| 6,083,353 A | 7/2000 | Alexander, Jr. | |
| 6,086,528 A | 7/2000 | Adair | |
| 6,104,334 A | 8/2000 | Allport | |
| 6,106,457 A | 8/2000 | Perkins et al. | |
| 6,139,489 A | 10/2000 | Wampler et al. | |
| 6,141,037 A * | 10/2000 | Upton ................. | A61B 1/00016 128/908 |
| 6,141,052 A | 10/2000 | Fukumitsu et al. | |
| 6,147,366 A | 11/2000 | Drottar et al. | |
| 6,154,254 A | 11/2000 | Hawkins et al. | |
| 6,172,950 B1 | 1/2001 | Tanaka | |
| 6,177,950 B1 | 1/2001 | Robb | |
| 6,184,804 B1 | 2/2001 | Harrison | |
| 6,190,877 B1 | 2/2001 | Adair | |
| 6,211,904 B1 | 4/2001 | Adair et al. | |
| 6,219,560 B1 | 4/2001 | Erkkilä et al. | |
| 6,219,793 B1 | 4/2001 | Li et al. | |
| 6,232,589 B1 | 5/2001 | Pace et al. | |
| 6,232,937 B1 | 5/2001 | Jacobsen et al. | |
| 6,243,131 B1 | 6/2001 | Martin | |
| 6,275,255 B1 | 8/2001 | Adair et al. | |
| 6,310,642 B1 | 10/2001 | Adair et al. | |
| 6,316,215 B1 | 11/2001 | Adair et al. | |
| 6,359,837 B1 | 3/2002 | Tsukamoto | |
| 6,370,282 B1 | 4/2002 | Pavley et al. | |
| 6,413,209 B1 | 7/2002 | Thompson | |
| 6,417,882 B1 | 7/2002 | Mahant-Shetti | |
| 6,424,369 B1 | 7/2002 | Adair et al. | |
| 6,452,626 B1 | 9/2002 | Adair et al. | |
| 6,507,336 B1 | 1/2003 | Lunsford | |
| 6,510,325 B1 | 1/2003 | Mack, II et al. | |
| 6,525,715 B2 | 2/2003 | Uchiyama et al. | |
| 6,526,653 B1 | 3/2003 | Glenn et al. | |
| 6,552,746 B1 | 4/2003 | Yang et al. | |
| 6,561,669 B2 | 5/2003 | Naghi et al. | |
| 6,658,272 B1 | 12/2003 | Lenchik et al. | |
| 6,659,940 B2 | 12/2003 | Adler | |
| 6,729,726 B2 | 5/2004 | Miller et al. | |
| 6,730,900 B2 | 5/2004 | Hsish et al. | |
| 6,750,037 B2 | 6/2004 | Adair et al. | |
| 6,753,160 B2 | 6/2004 | Adair | |
| 6,761,561 B2 | 7/2004 | Mandelkern et al. | |
| 6,809,358 B2 | 10/2004 | Hsieh et al. | |
| 6,862,036 B2 | 3/2005 | Adair et al. | |
| 6,918,872 B2 | 7/2005 | Yokoi et al. | |
| 6,982,740 B2 | 1/2006 | Adair et al. | |
| 6,982,742 B2 | 1/2006 | Adair et al. | |
| 6,984,498 B2 | 1/2006 | Adair | |
| 6,992,699 B1 | 1/2006 | Vance et al. | |
| 7,002,621 B2 | 2/2006 | Adair et al. | |
| 7,030,904 B2 | 4/2006 | Adair et al. | |
| 7,038,716 B2 | 5/2006 | Klein et al. | |
| 7,067,276 B2 | 6/2006 | Adair | |
| 7,110,808 B2 | 9/2006 | Adair | |
| 7,649,548 B1 | 1/2010 | Knuutila et al. | |
| 8,885,034 B2 * | 11/2014 | Adair et al. .......... | 348/76 |
| 2001/0034222 A1 | 10/2001 | Roustaei et al. | |
| 2002/0163578 A1 | 11/2002 | Adair et al. | |

(56) References Cited

U.S. PATENT DOCUMENTS

| | | |
|---|---|---|
| 2006/0022234 A1 | 2/2006 | Adair et al. |
| 2007/0043289 A1 | 2/2007 | Adair |
| 2011/0034769 A1* | 2/2011 | Adair et al. ............... 600/110 |
| 2013/0144122 A1* | 6/2013 | Adair et al. ............... 600/110 |

FOREIGN PATENT DOCUMENTS

| | | |
|---|---|---|
| AU | 7004201 | 2/2002 |
| AU | 2001293121 | 3/2003 |
| AU | 2001293138 | 3/2003 |
| CA | 2301714 | 4/1999 |
| CA | 2345811 | 2/2001 |
| CA | 2322124 | 4/2001 |
| CA | 2368245 | 8/2001 |
| DE | 19950840 | 5/2000 |
| DE | 10028080 | 2/2001 |
| DE | 10028081 | 2/2001 |
| DE | 19947875 | 5/2001 |
| DE | 60117989 | 12/2006 |
| EP | 0492349 | 7/1992 |
| EP | 0932302 | 7/1999 |
| EP | 0957448 | 11/1999 |
| EP | 1104182 | 5/2001 |
| EP | 1117324 | 7/2001 |
| EP | 1164916 | 1/2002 |
| EP | 1310090 | 5/2003 |
| EP | 1029356 | 7/2005 |
| EP | 1300001 | 3/2006 |
| EP | 1575092 | 8/2008 |
| JP | S59-88135 | 5/1984 |
| JP | S60-74880 | 4/1985 |
| JP | S61-254917 | 11/1986 |
| JP | S64-86677 | 3/1989 |
| JP | H03-109891 | 5/1991 |
| JP | H04-152773 | 5/1992 |
| JP | H06-142029 | 5/1994 |
| JP | H06-261312 | 9/1994 |
| JP | H06-335450 | 12/1994 |
| JP | H08-280611 | 10/1996 |
| JP | H08-321863 | 12/1996 |
| JP | H09-46566 | 2/1997 |
| JP | H11-032379 | 2/1999 |
| JP | H11-275416 | 10/1999 |
| JP | 3082825 | 1/2002 |
| JP | 2003-521324 | 7/2003 |
| JP | 2004-512704 | 4/2004 |
| JP | 2004-536467 | 12/2004 |
| JP | 3842041 | 11/2006 |
| JP | 4312800 | 8/2009 |
| JP | 4488172 | 6/2010 |
| WO | WO 91/12044 | 8/1991 |
| WO | WO 93/15648 | 8/1993 |
| WO | WO 97/15144 | 4/1997 |
| WO | WO 97/26744 | 7/1997 |
| WO | WO 98/11816 | 3/1998 |
| WO | WO 98/19435 | 5/1998 |
| WO | WO 99/18613 | 4/1999 |
| WO | WO 00/36583 | 6/2000 |
| WO | WO 01/08549 | 2/2001 |
| WO | WO 01/45793 | 6/2001 |
| WO | WO 01/48477 | 7/2001 |
| WO | WO 01/56458 | 8/2001 |
| WO | WO 02/05546 | 1/2002 |
| WO | WO 02/09023 | 1/2002 |
| WO | WO 02/15567 | 2/2002 |
| WO | WO 03/015619 | 2/2003 |
| WO | WO 03/019660 | 3/2003 |
| WO | WO 03/019940 | 3/2003 |
| WO | WO 03/030525 | 4/2003 |

OTHER PUBLICATIONS

"Ericsson Unveils the T68, a GPRS Phone With MMS, a Color Display and Bluetooth," Telefonaktiebolaget LM Ericsson, Mar. 21, 2001, [retrieved on Mar. 21, 2001], 3 pages. Retrieved from: http://biz.yahoo.com/bw/010321/2239.html.

"Europe gains as consumer electronics leader," EETimes, Jun. 28, 2000, 4 pages. Retrieved from: www.eetimes.com/document.asp?doc_id=1224679.

"Nokia and Fujifilm to cooperate in developing Bluetooth technology to send digital still images and applications technology," Nokia Corp., Feb. 14, 2000, [retrieved on Jan. 5, 2001], 1 page. Retrieved from http://press.nokia.com/PR/20002/775373_5.html.

"Pantech Breeze C520 User Manual," Pantech Wireless, Inc., 2008, 94 pages.

"Sanyo Semiconductor Adds Bluetooth Connectivity to Digital Camera Chips With Tality Intellectual Property," Tality Corp., Dec. 5, 2000, [retrieved on Jun. 6, 2001], 2 pages. Retrieved from: www.tality.com/news_events/release/pr-bluetoooth_sanyo.html.

"Silicon Eyes", Business Week, Oct. 11, 1998, 3 pages.

Wireless Pictures: Part of a New Technology, Eastman Kodak Co., 2001, [retrieved on Jun. 26, 2001], 4 pages. Retrieved from: www.kodak.com/US/en/corp/researchDevelopment/technologyReatures.wireless.shtml.

Armstrong et al., "NASA's Tiny Camera Has a Wide-Angle Future"; Business Week, Mar. 6, 1995, 3 pages.

Device named "Digital Doc Intra Oral Camera"; sold by Digital Doc, Inc., Folsom, CA date unknown, [retrieved on Aug. 13, 2001], 3 pages.

Drexler, "See and say: Wireless video phone on the way," CNN.com, Sep. 27, 1999 [retrieved on Jul. 6, 2001], 4 pages. Retrieved from: wvvw.cnn.com/TECH/computing/9909/27/nec.vid.phone.idg/.

Hsieh et al. "Low-Power Parallel Video Compression Architecture for a Single-Chip Digital CMOS Camera," Journal of VLSI Signal Processing Systems for Signal, Image, and Video Technology, 1999, vol. 21, Iss. 3, pp. 195-207.

Jakl, "Why CMOS Image Sensors are Poised to Surpass CCDs," International IC '99, Conference Proceedings, 1999, pp. 64-71.

Lockyer, "Applications Hold the Key to Imager Choice"; Photonics Spectra, Mar. 1997, pp. 80-90.

Mendis et al., "CMOS Active Pixel Image Sensor," IEEE Transactions on Electron Devices, 1994, vol. 41, Iss. 3, 7 pages.

Meyerson, "Kids, I'm dialing Grandma now, so stand straight . . . and smile," Denver Rocky Mountain News, Sep. 5, 2000, 1 page.

Nishikawa et al., "A 60MHz 240mW MPEG-4 Video-Phone LSI with 16Mb Embedded DRAM," IEEE International Solid-State Circuits Conference, 2000, pp. 230-231.

Nixon et al., "256x256 CMOS Active Pixel Sensor Camera-on-a-Chip," IEEE Journal of Solid-State Circuits, 1996, vol. 31, Iss. 12, pp. 2046-2050.

Nixon et al., "Active-Pixel Image Sensor Integrated With Readout Circuits"; Nasa Tech Briefs, Oct. 1996, 2 pages.

Parulski et al. "The Continuing Evolution of Digital Cameras and Digital Photography Systems," Proceedings of the IEEE International Symposium on Circuits and Systems, 2000, vol. 5, pp. 101-104.

Takahashi et al., "A scalable MPEG-4 video codec architecture for IMT-2000 multimedia applications," Proceedings of the IEEE International Symposium on Circuits and Systems, 2000, vol. 2, pp. 188-191.

Tariq et al., "Robust and scalable matching pursuits video transmission using the Bluetooth air interface standard," IEEE Transactions on Consumer Electronics, 2000, vol. 46, No. 3, pp. 673-681.

Zarnowski et al., "Imaging Options Expand With CMOS Technology"; Laser Focus World, Jun. 1997, 5 pages.

International Search Report for International (PCT) Patent Application No. PCT/US98/19379 mailed Feb. 1, 1999, 3 pages.

Written Opinion for International (PCT) Patent Application No. PCT/US98/19379 mailed Jul. 1, 1999, 8 pages.

International Preliminary Examination Report for International (PCT) Patent Application No. PCT/US98/19379 mailed Nov. 5, 1999, 8 pages.

Official Action for European Patent Application No. 98948297.1 dated Mar. 28, 2002, 4 pages.

European Search Report for European Patent Application No. 05010986.7 dated Apr. 5, 2006, 3 pages.

(56) References Cited

OTHER PUBLICATIONS

International Search Report for International (PCT) Patent Application No. PCT/US00/40518 mailed Nov. 20, 2000, 3 pages.
International Search Report for International (PCT) Patent Application No. PCT/US00/10118 mailed Oct. 25, 2000, 6 pages.
Official Action for Canadian Patent Application No. 2,368,245 dated May 3, 2006, 5 pages.
European Search Report for European Patent Application No. 00928180.9 dated Feb. 1, 2005, 2 pages.
International Search Report for International (PCT) Patent Application No. PCT/US01/19854 mailed Oct. 26, 2001, 3 pages.
Written Opinion for International (PCT) Patent Application No. PCT/US01/19854 mailed Jan. 11, 2002, 2 pages.
International Preliminary Examination Report for International (PCT) Patent Application No. PCT/US01/19854 dated Nov. 28, 2002, 6 pages.
Official Action for European Patent Application No. 01948574.7 dated May 24, 2004, 3 pages.
International Search Report for International (PCT) Patent Application No. PCT/US01/19855 mailed Nov. 20, 2001, 3 pages.
Written Opinion for International (PCT) Patent Application No. PCT/US01/19855 mailed May 7, 2002, 5 pages.
International Preliminary Examination Report for International (PCT) Patent Application No. PCT/US01/19855 dated Jul. 1, 2004, 6 pages.
Official Action (English translation) for Japanese Patent Application No. 2002-520552 mailed Oct. 17, 2006, 2 pages.
International Search Report for International (PCT) Patent Application No. PCT/US01/30155 mailed Jul. 16, 2002, 3 pages.
International Search Report for International (PCT) Patent Application No. PCT/US01/30154 mailed Jan. 28, 2003, 5 pages.
International Search Report for International (PCT) Patent Application No. PCT/US01/44069 mailed Aug. 1, 2002, 3 pages.
Official Action for U.S. Appl. No. 08/944,322 mailed Jul. 30, 1998, 15 pages.
Official Action for U.S. Appl. No. 08/944,322 mailed Dec. 9, 1998, 11 pages.
Notice of Allowance for U.S. Appl. No. 08/944,322 mailed Mar. 4, 1999, 4 pages.
Official Action for U.S. Appl. No. 08/976,976 mailed Jul. 22, 1998, 6 pages.
Official Action for U.S. Appl. No. 08/976,976 mailed Dec. 9, 1998, 7 pages.
Notice of Allowance for U.S. Appl. No. 08/976,976 mailed Mar. 4, 1999, 5 pages.
Official Action for U.S. Appl. No. 09/175,685 mailed Aug. 6, 1999, 23 pages.
Official Action for U.S. Appl. No. 09/175,685 mailed Nov. 4, 1999, 12 pages.
Notice of Allowance for U.S. Appl. No. 09/175,685 mailed Nov. 22, 1999, 4 pages.
Official Action for U.S. Appl. No. 09/496,312 mailed Sep. 29, 2000, 14 pages.
Notice of Allowance for U.S. Appl. No. 09/496,312 mailed Apr. 6, 2001, 5 pages.
Official Action for U.S. Appl. No. 09/368,246 mailed Nov. 30, 2000, 11 pages.
Notice of Allowance for U.S. Appl. No. 09/368,246 mailed Jun. 12, 2001, 3 pages.
Notice of Allowance for U.S. Appl. No. 09/544,528 mailed Dec. 4, 2000, 5 pages.
Official Action for U.S. Appl. No. 10/198,189 mailed Jun. 2, 2003, 15 pages.
Notice of Allowance for U.S. Appl. No. 10/198,189 mailed Sep. 27, 2004, 7 pages.
Official Action for U.S. Appl. No. 10/171,906 mailed Mar. 12, 2003, 19 pages.
Official Action for U.S. Appl. No. 09/929,531, mailed Dec. 29, 2004.
Notice of Allowance for U.S. Appl. No. 09/929,531, mailed Sep. 16, 2005.
Official Action for U.S. Appl. No. 11/245,960, mailed Apr. 28, 2010 (Restriction Requirement).
Official Action for U.S. Appl. No. 12/889,287, mailed Nov. 7, 2012, 9 pages.
Official Action for U.S. Appl. No. 09/934,201 mailed Dec. 16, 2004, 10 pages.
Notice of Allowance for U.S. Appl. No. 09/934,201 mailed Jul. 13, 2005, 6 pages.
Official Action for U.S. Appl. No. 09/935,993 mailed Dec. 17, 2004, 9 pages.
Notice of Allowance for U.S. Appl. No. 09/935,993 mailed Dec. 17, 2004, 6 pages.
Official Action for U.S. Appl. No. 09/971,749 mailed Jan. 5, 2005, 15 pages.
Notice of Allowance for U.S. Appl. No. 09/971,749 mailed Sep. 16, 2005, 6 pages.
Official Action for U.S. Appl. No. 13/732,908 mailed Jul. 26, 2013, 10 pages.
Official Action for U.S. Appl. No. 13/732,908 mailed Apr. 3, 2014, 7 pages.
Notice of Allowance for U.S. Appl. No. 13/732,908 mailed Jul. 3, 2014 8 pages.

* cited by examiner

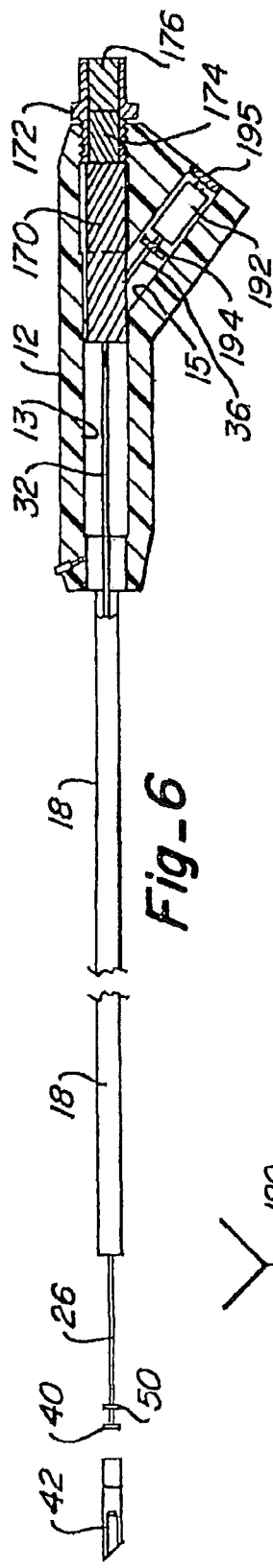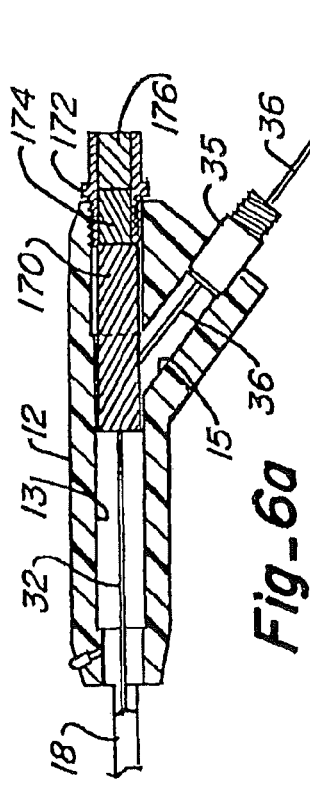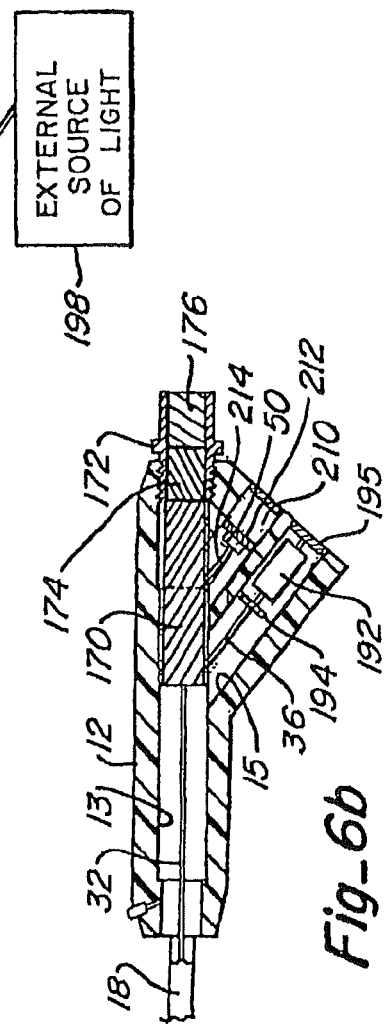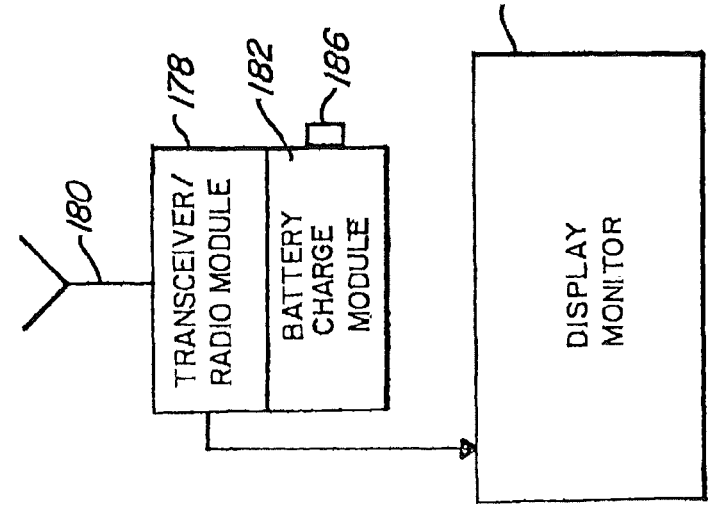

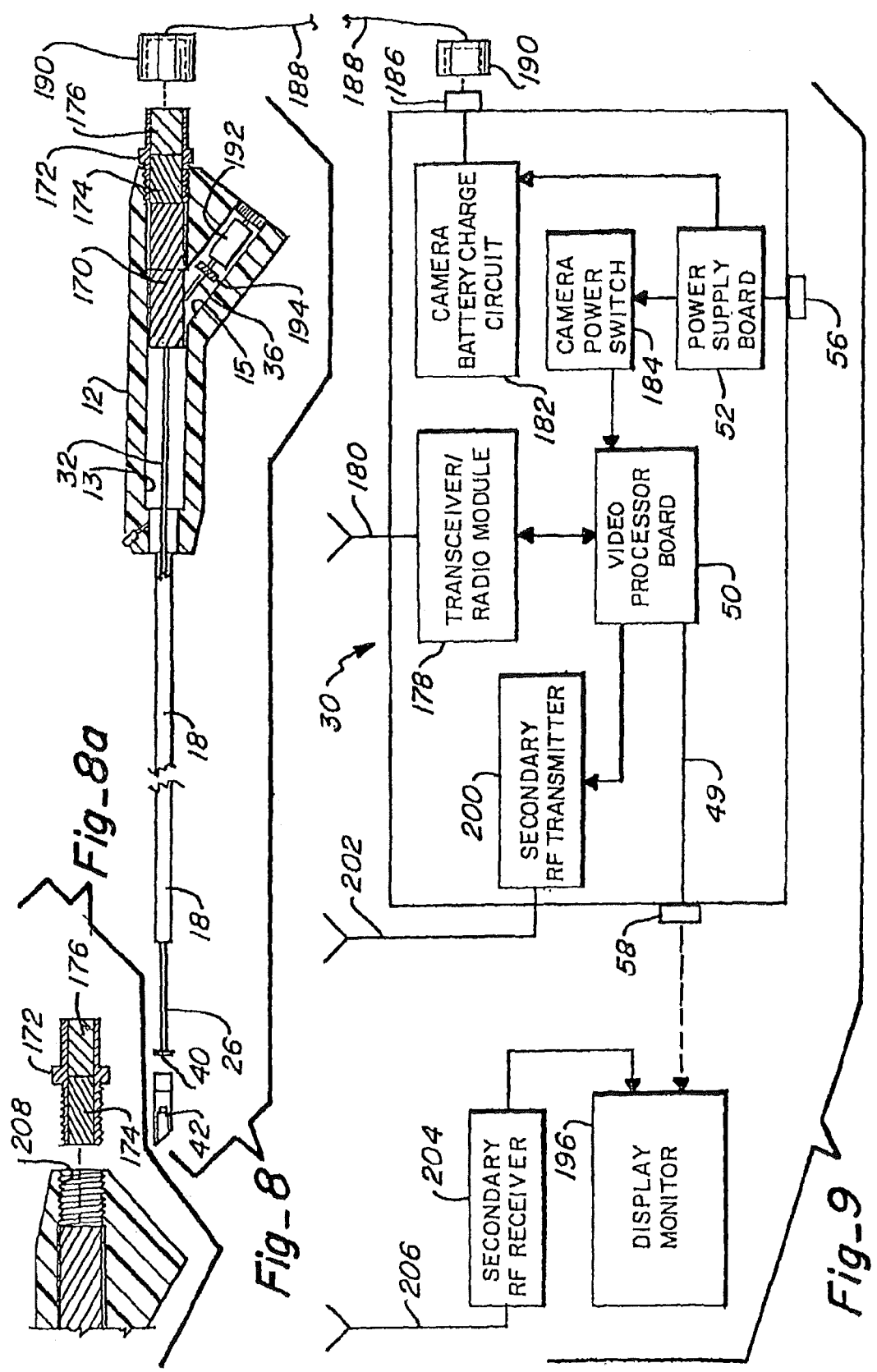

REDUCED AREA IMAGING DEVICE INCORPORATED WITHIN ENDOSCOPIC DEVICES

CROSS REFERENCE TO RELATED APPLICATIONS

This application is a continuation of U.S. Ser. No. 13/732,908 filed on Jan. 2, 2013, which is a continuation of U.S. Ser. No. 12/889,287 filed on Sep. 23, 2010, which is a continuation-in-part of U.S. Ser. No. 11/245,960, filed on Oct. 6, 2005, which is a continuation of U.S. patent application Ser. No. 09/929,531, filed on Aug. 13, 2001, which is a continuation-in-part of U.S. Ser. No. 09/496,312 filed on Feb. 1, 2000, now U.S. Pat. No. 6,275,255, which is a continuation of U.S. Ser. No. 09/175,685 filed Oct. 20, 1998, now U.S. Pat. No. 6,043,839, which is a continuation-in-part of U.S. Ser. No. 08/944,322, filed Oct. 6, 1997, now U.S. Pat. No. 5,929,901.

FIELD OF THE INVENTION

This invention relates to solid state image sensors incorporated within wireless endoscopes, and more particularly, to solid state image sensors which are incorporated within wireless endoscopes that wirelessly transmit video images for viewing.

BACKGROUND OF THE INVENTION

In recent years, endoscopic surgery has become the accepted standard for conducting many types of surgical procedures, both in the medical and dental arenas. The availability of imaging devices enabling a surgeon or dentist to view a particular surgical area through a small diameter endoscope which is introduced into small cavities or openings in the body results in much less patient trauma as well as many other advantages.

In many hospitals, the rod lens endoscope is still used in endoscopic surgery. The rod lens endoscope includes a very precise group of lenses in an elongate and rigid tube which are able to accurately transmit an image to a remote camera in line with the lens group. The rod lens endoscope, because of its cost of manufacture, failure rate, and requirement to be housed within a rigid and straight housing, is being increasingly replaced by solid state imaging technology which enables the image sensor to be placed at the distal tip of the investigating device. The three most common solid state image sensors include charged coupled devices (CCD), charge injection devices (CID) and photo diode arrays (PDA). In the mid-1980s, complementary metal oxide semiconductors (CMOS) were developed for industrial use. CMOS imaging devices offer improved functionality and simplified system interfacing. Furthermore, many CMOS imagers can be manufactured at a fraction of the cost of other solid state imaging technologies.

One particular advance in CMOS technology has been in the active pixel-type CMOS imagers which consist of randomly accessible pixels with an amplifier at each pixel site. One advantage of active pixel-type imagers is that the amplifier placement results in lower noise levels than CCDs or other solid state imagers. Another major advantage is that these CMOS imagers can be mass produced on standard semiconductor production lines. One particularly notable advance in the area of CMOS imagers including active pixel-type arrays is the CMOS imager described in U.S. Pat. No. 5,471,515 to Fossum, et al. This CMOS imager can incorporate a number of other different electronic controls that are usually found on multiple circuit boards of much larger size. For example, timing circuits, and special functions such as zoom and anti jitter controls can be placed on the same circuit board containing the CMOS pixel array without significantly increasing the overall size of the host circuit board. Furthermore, this particular CMOS imager requires 100 times less power than a CCD-type imager. In short, the CMOS imager disclosed in Fossum, et al. has enabled the development of a "camera on a chip."

Passive pixel-type CMOS imagers have also been improved so that they too can be used in an imaging device which qualifies as a "camera on a chip." In short, the major difference between passive and active CMOS pixel arrays is that a passive pixel-type imager does not perform signal amplification at each pixel site. One example of a manufacturer which has developed a passive pixel array with performance nearly equal to known active pixel devices and being compatible with the read out circuitry disclosed in the U.S. Pat. No. 5,471,515 is VLSI Vision, Ltd., 1190 Saratoga Avenue, Suite 180, San Jose, Calif. 95129. A further description of this passive pixel device may be found in applicant's U.S. Pat. No. 5,986,693 entitled "Reduced Area Imaging Devices Incorporated Within Surgical Instruments," which is hereby incorporated by reference.

In addition to the active pixel-type CMOS imager which is disclosed in U.S. Pat. No. 5,471,515, there have been developments in the industry for other solid state imagers which have resulted in the ability to have a "camera on a chip." For example, Suni Microsystems, Inc. of Mountain View, Calif., has developed a CCD/CMOS hybrid which combines the high quality image processing of CCDs with standard CMOS circuitry construction. In short, Suni Microsystems, Inc. has modified the standard CMOS and CCD manufacturing processes to create a hybrid process providing CCD components with their own substrate which is separate from the P well and N well substrates used by the CMOS components. Accordingly, the CCD and CMOS components of the hybrid may reside on different regions of the same chip or wafer. Additionally, this hybrid is able to run on a low power source (5 volts) which is normally not possible on standard CCD imagers which require 10 to 30 volt power supplies. A brief explanation of this CCD/CMOS hybrid can be found in the article entitled "Startup Suni Bets on Integrated Process" found in *Electronic News*, Jan. 20, 1997 issue. This reference is hereby incorporated by reference for purposes of explaining this particular type of imaging processor.

Another example of a recent development in solid state imaging is the development of a CMOS imaging sensor which is able to achieve analog to digital conversion on each of the pixels within the pixel array. This type of improved CMOS imager includes transistors at every pixel to provide digital instead of analog output that enable the delivery of decoders and sense amplifiers much like standard memory chips. With this new technology, it may, therefore, be possible to manufacture a true digital "camera on a chip." This CMOS imager has been developed by a Stanford University joint project and is headed by Professor Abbas el-Gamal.

A second approach to creating a CMOS-based digital imaging device includes the use of an over-sample converter at each pixel with a one bit comparator placed at the edge of the pixel array instead of performing all of the analog to digital functions on the pixel. This new design technology has been called MOSAD (multiplexed over sample analog to digital) conversion. The result of this new process is low power usage, along with the capability to achieve enhanced dynamic range, possibly up to 20 bits. This process has been developed by Amain Electronics of Simi Valley, Calif. A brief description of both of the processes developed by Stanford University and Amain Electronics can be found in an article entitled "A/D Conversion Revolution for CMOS Sensor?," September 1998 issue of *Advanced Imaging*. This reference is also hereby incorporated by reference for purposes of explaining these particular types of imaging processors.

The above-mentioned developments in solid state imaging technology have shown that "camera on a chip" devices will continue to be enhanced not only in terms of the quality of imaging which may be achieved, but also in the specific construction of the devices which may be manufactured by new breakthrough processes.

Although the "camera on a chip" concept is one which has great merit for application in many industrial areas, a need still exists for a reduced area imaging device which can be used in even the smallest type of endoscopic instruments in order to view areas in the body that are particularly difficult to access, and to further minimize patient trauma by an even smaller diameter invasive instrument.

It is one general object of this invention to provide a wireless endoscope incorporating reduced area imaging devices which take advantage of "camera on a chip" technology, but rearrange the circuitry in a stacked relationship so that there is a minimum profile presented when used within a surgical instrument or other investigative device. It is another object of this invention to provide a wireless endoscope utilizing low cost imaging devices which may be "disposable." It is yet another object of this invention to provide reduced area imaging devices capable of wireless communications which may be used in conjunction with standard endoscopes by placing the imaging device through channels which normally receive other surgical devices, or receive liquids or gases for flushing a surgical area. It is yet another object of this invention to provide a surgical device with imaging capability which may be battery powered and may wirelessly communicate for viewing video images.

In addition to the intended use of the wireless endoscope with respect to surgical procedures conducted by medical doctors, it is also contemplated that the invention described herein has great utility with respect to oral surgery and general dental procedures wherein a very small imaging device can be used to provide an image of particularly difficult to access locations. Additionally, while the foregoing invention has application with respect to the medical and dental fields, it will also be appreciated by those skilled in the art that the small size of the imaging device set forth herein coupled with the wireless communication feature can be applied to other functional disciplines wherein the imaging device can be used to view difficult to access locations for industrial equipment and the like. Therefore, the imaging device of this invention could be used to replace many industrial boroscopes.

The "camera on a chip" technology can be furthered improved with respect to reducing its profile area and incorporating such a reduced area imaging device into very small investigative instruments which can be used in the medical, dental, or other industrial fields.

SUMMARY OF THE INVENTION

In accordance with the present invention, reduced area imaging devices are provided. The term "imaging device" as used herein describes the imaging elements and processing circuitry which is used to produce a video signal which may be accepted by a standard video device such as a television or video monitor accompanying a personal computer. The term "image sensor" as used herein describes the components of a solid state imaging device which captures images and stores them within the structure of each of the pixels in the array of pixels found in the imaging device. As further discussed below, the timing and control circuits can be placed either on the same planar structure as the pixel array, in which case the image sensor can also be defined as an integrated circuit, or the timing and control circuitry can be placed remote from the pixel array. The terms "signal" or "image signal" as used herein, and unless otherwise more specifically defined, refer to an image which at some point during its processing by the imaging device, is found in the form of electrons which have been placed in a specific format or domain. The term "processing circuitry" as used herein refers to the electronic components within the imaging device which receive the image signal from the image sensor and ultimately place the image signal in a usable format. The terms "timing and control circuits" or "circuitry" as used herein refer to the electronic components which control the release of the image signal from the pixel array.

In a first embodiment of the endoscope, the imaging device utilizes wired connections for interconnecting the various elements of the imaging device, and utilizes wired connections for transferring video images to a video display.

In a second embodiment of the endoscope, a wireless communications means may be used to allow various elements of the imaging device to communicate with one another. Transfer of video images to a video display can also be achieved by the wireless communications means. Thus in the second embodiment, the endoscope does not have to be physically connected to other operating room equipment which greatly enhances the ease of using the wireless endoscope. Particularly in endoscopic procedures which are conducted in hard to reach locations within the body, a wireless endoscope is advantageous because there are no trailing cables or sterile drapes which otherwise complicate maneuvering of the endoscope. In general, enhanced maneuverability of the endoscope is provided by the wireless communications.

One particularly advantageous wireless technology usable with the endoscope of this invention is known as "Bluetooth". Another recent wireless technology which is usable with the invention is a wireless protocol known as "IEEE 802.15.13". This wireless standard is developing under the joint efforts of Kodak, Motorola, Cisco and the International Electronic and Electrical Engineers Standards Association (IEEE) Wireless Personal Area Network Working Group (WPAN). Bluetooth technology provides a universal radio interface in the 2.4 GHz frequency band that enables portable electronic devices to connect and communicate wirelessly via short-range ad hoc networks. Bluetooth radios operate in an unlicensed Instrumentation, Scientific, Medical (ISM) band at 2.4 Ghz. Bluetooth is a combination of circuit and packet switching. Slots can be reserved for synchronous packets. Each packet is transmitted in a different hop frequency. A packet nominally covers a single slot, but can be extended to cover up to five slots. Bluetooth can support an asynchronous data channel, up to three simultaneous synchronous voice channels, or a channel that simultaneously supports asynchronous data and synchronous voice. Spectrum spreading is accomplished by frequency hopping 79 hops displaced by 1 MHZ starting at 2.402 Ghz and stopping at 2.480 GHz. The maximum frequency hopping rate is 1600 hops per second. The nominal link range is 10 centimeters to 10 meters, but can be extended to more than 100 meters by increasing the transmit power. A shaped binary FM modulation is applied to minimize transceiver complexity. The gross data rate is 1 Mb/second. A time division multiplex scheme is used for full-duplex transmission. Additional information describing the Bluetooth global specification is found on the world wide web at www.bluetooth.com. Additional information regarding the technical specification for the IEEE 802.15.13 standard may be found www.ieee802.org/15 under the link for the Task Force Three (TG3). The content of both of these websites is hereby incorporated by reference for purposes of disclosing these types of communication standards.

In a first arrangement of the imaging device, the image sensor, with or without the timing and control circuitry, may be placed at the distal tip of the endoscopic instrument while the remaining processing circuitry may be found in a small remote control box which may wirelessly communicate with the image sensor.

In a second arrangement of the imaging device, the image sensor and the processing circuitry may all be placed in a stacked arrangement of circuit boards and positioned at the distal tip of the endoscopic instrument. In this second arrangement, the pixel array of the image sensor may be placed by itself on its own circuit board while the timing and control circuitry and processing circuitry are placed on one or more other circuit boards. Alternatively, the circuitry for timing and control may be placed with the pixel array on one circuit board, while the remaining processing circuitry can be placed on one or more of the other circuit boards.

In another alternative arrangement, the imaging device may be adapted for use with a standard rod lens endoscope wherein the imaging device is placed within a standard camera housing which is configured to connect to a standard "C" or "V" mount connector.

In yet another arrangement, the timing and control circuitry and/or the processing circuitry may be placed in the handle of the endoscope. It is even completed that some circuitry could be placed in the handle of the endoscope while remaining circuitry is placed within the remote control box. Because of the small size of the elements making up the imaging device coupled with the ability to provide wireless communications between the elements, great diversification is provided for the combinations of locations at which the different elements may be employed.

A simplified endoscope may be used which includes a very small diameter tubular portion which is inserted within the patient. The tubular portion may be made of a flexible material having a central lumen or opening therein for receiving the elements of the imaging device. The tubular portion may be modified to include an additional concentric tube placed within the central lumen and which enables a plurality of light fibers to be placed circumferentially around the periphery of the distal end of the tubular portion. Additionally, control wires may extend along the tubular portion in order to make the endoscope steerable. The material used to make the endoscope can be compatible with any desired sterilization protocol, or the entire endoscope can be made sterile and disposable after use.

In the second embodiment of the endoscope wherein processing circuitry is housed within the endoscope, and for the arrangement of the imaging device which calls for the array of pixels and the timing and control circuitry to be placed on the same circuit board, only one conductor is required in order to electrically transfer the image signal to the processing circuitry. In the other configuration of the imaging device wherein the timing and control circuits are incorporated onto other circuit boards, a plurality of connections are required in order to connect the timing and control circuitry to the pixel array and the one conductor is also required to transfer the image signal.

In each of the different arrangements of the imaging device where circuitry is housed in the handle of the endoscope, the handle can have one or more channels or bores for making space available for such circuitry.

Thus, the wireless communications made integral with the endoscope of the second embodiment provides an improved endoscope wherein the improvement comprises variations of wireless communications for transmission of image signals that are viewed on a desired video display.

In another aspect of the invention, the imaging device is housed within an endoscopic instrument in which the endoscope is steerable by incorporating a steering connector assembly located near the imaging device. The connector assembly is constructed so that it does not enlarge the profile of the capsule that houses the imaging device, yet the connector assembly facilitates precise and accurate control of the distal end of the endoscope with a four-way deflection capability. More specifically, the image sensor has a frontal profile defined by a length and width dimension, and the connector assembly does not extend beyond this frontal profile or a slightly larger frontal profile defined by the length and width dimension of the capsule.

The connector assembly has dual functionality in providing a means to anchor the distal ends of the steering wires as well as to provide a structure for attaching the electrical leads of an image/power cable to electrical traces housed in the connector assembly that extend to electrically contact electrical connection points on the imaging device.

BRIEF DESCRIPTION OF THE DRAWINGS

FIG. 3a is a fragmentary cross-sectional view of the image sensor incorporated with a standard camera housing for connection to a rod lens endoscope;

FIG. 3b is a fragmentary cross-sectional view of the imaging device incorporated within the camera housing of FIG. 3a;

FIG. 3c is a fragmentary cross-sectional view similar to that of FIG. 3b illustrating a battery as an alternate source of power;

FIG. 6 is a fragmentary cross-sectional view of an endoscope in the second embodiment wherein image signals in a desired video ready format are wirelessly transmitted to a remote video display monitor for viewing by a user;

FIG. 6a is another fragmentary cross-sectional view of the endoscope of FIG. 6 showing an alternate source of light in the form of a fiber optic cable connected to an external light source;

FIG. 6b is another fragmentary cross-sectional view of the endoscope of FIG. 6 showing processing circuitry incorporated within the handle of the endoscope as opposed to the circuitry placed within the tubular portion of the endoscope;

FIG. 7 illustrates a transceiver radio module which receives image signals transmitted by the wireless endoscope of FIG. 6\FIG. 6a, and conditions the received image signals for direct reception by a display monitor;

FIG. 8 illustrates another endoscope of the second embodiment wherein some image signal processing is conducted remote from the endoscope;

FIG. 8a illustrates a removable battery housing which may be recharged by removing the housing and plugging it into the recharge receptacle on the control box of FIG. 9; and FIG. 9 illustrates the arrangement of the imaging device which incorporates the control box wherein image signals from the endoscope in FIG. 8 are in a first or pre-format and are transmitted wirelessly to the control box, circuitry in the control box processes the image signals in a second or final format, and the control box then wirelessly transmits the image signals to a secondary receiver which receives the image signals and conditions the image signals for direct reception by the display monitor.

BEST MODE FOR CARRYING OUT THE INVENTION

Figure 1:
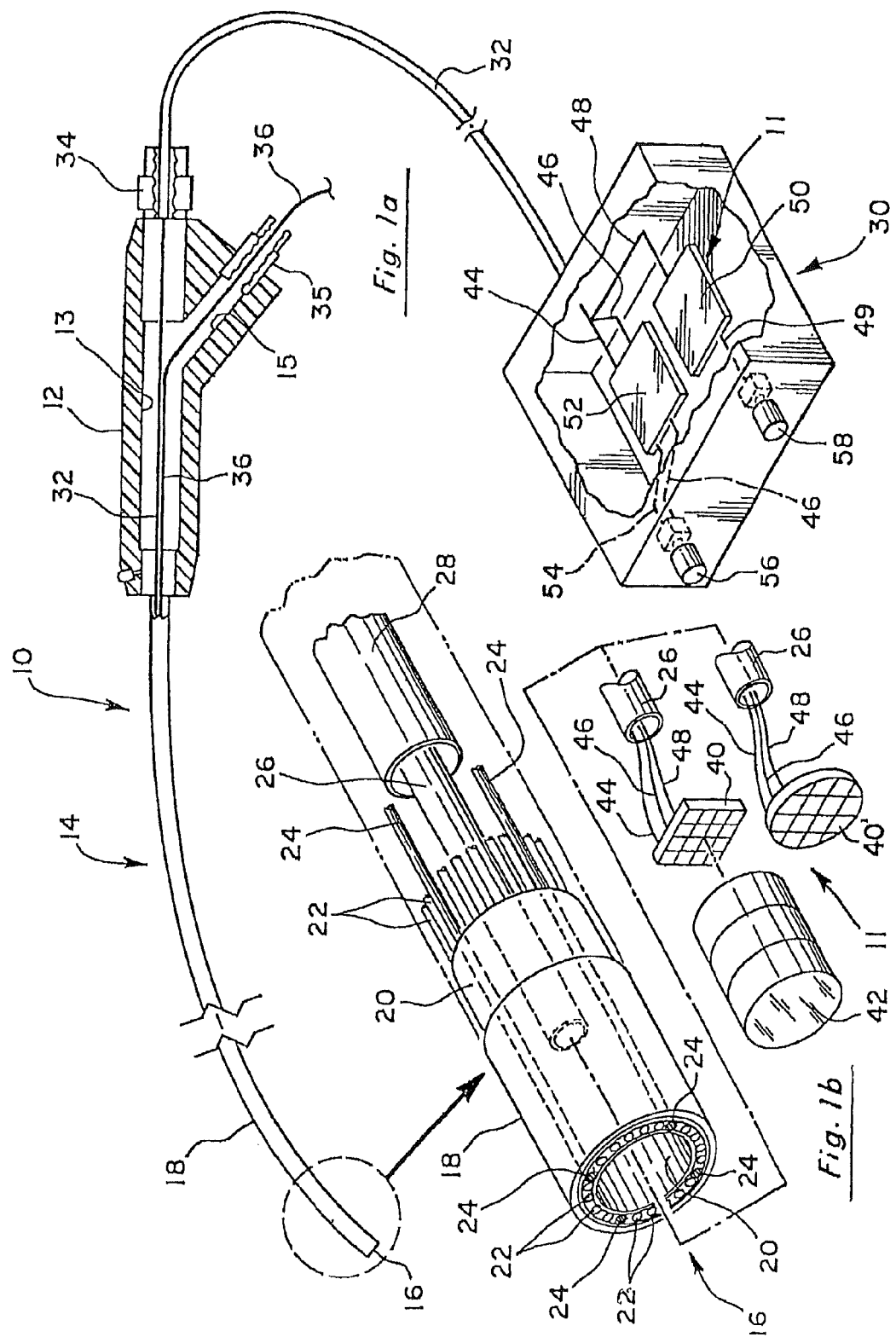
FIG. 1a illustrates a first arrangement of the imaging device including a fragmentary cross-sectional view of a generic endoscopic instrument in the first embodiment, and a fragmentary perspective view of a control box, the endoscope and control box each incorporating elements of a reduced area imaging device.
FIG. 1b is an enlarged fragmentary partially exploded perspective view of the distal end of the endoscopic instrument specifically illustrating the arrangement of the image sensor with respect to the other elements of the tubular portion of the endoscope.

In accordance with one arrangement of the imaging device as shown in FIG. 1a, an endoscope 10 in the first embodiment is provided which incorporates a reduced area imaging device 11, shown in FIG. 1b. As further discussed below, the elements of the imaging device may all be found at one location or the elements may be separated from one another and interconnected by the appropriate cable(s). The array of pixels making up the image sensor captures images and stores them in the form of electrical energy by conversion of light photons to electrons. This conversion takes place by the photo diodes in each pixel which communicate with one or more capacitors which store the electrons. The structure of the endoscope 10 in the first embodiment includes a flexible or rigid tubular portion 14 which is inserted into the body of the patient and is placed at the appropriate location for viewing a desired surgical area. The tubular portion 14 attaches at its proximal end to a handle portion 12 which may be grasped by a surgeon who is conducting the endoscopic procedure. The handle 12 may include a central lumen or channel 13 which receives one or more cables or other structures which extend to the distal end 16 of tubular portion 14. Handle portion 12 may further include a supplementary channel 15 which intersects with central channel 13 and which may provide another point of entry for other cables, fluids or operative instruments to be placed through the endoscope.

FIG. 1b illustrates the distal end of the endoscope 16. The distal end 16 may be characterized by an outer tube 18 which traverses the length of the tubular portion 14 and connects to the handle portion 12. Placed concentrically within the outer tube 18 may be one or more inner tubes 20. In FIG. 1b, the gap between inner tube 20 and outer tube 18 forms a space in which one or more light fibers 22 or control wires 24 may be placed. As well understood by those skilled in the art, a plurality of circumferentially spaced light fibers as illustrated in FIG. 1b can be used to illuminate the surgical site. Additionally, the control wires 24 may communicate with a control mechanism (not shown) integrated on the handle portion 12 for manipulating the distal end 16 of the endoscope in a desired direction. The flexible tubular portion 14 coupled with a steerable feature enables the endoscope to be placed within winding bodily passages or other locations difficult to reach within the body.

An image sensor 40 may be placed within the central channel defined by inner tube 20. In the configuration shown in FIG. 1b, a cable 26 is used to house the conductors which communicate with the image sensor 40. An intermediate support tube 28 may be placed concentrically outside of cable 26 and concentrically within inner tube 20 to provide the necessary support for the cable 26 as it traverses through the inner channel defined by inner tube 20. In lieu of support tube 28, other well-known means may be provided to stabilize the cable 26 such as clips or other fastening means which may attach to the inner concentric surface of inner tube 20.

A control box 30 may be placed remote from the endoscope 10. The control box 30 contains some of the processing circuitry which is used to process the image signal produced by image sensor 40. Therefore, the imaging device 11 as previously defined would include the processing circuitry within control box 30 and the image sensor 40 located at the distal tip of the endoscope. Control box 30 communicates with image sensor 40 by means of cable 32 which may simply be an insulated and shielded cable which houses therein cable 26. Cable 32 is stabilized with respect to the handle portion 12 by means of a fitting 34 which ensures that cable 32 cannot be inadvertently pushed or pulled within channel 13. Additionally, an additional fitting 35 may be provided to stabilize the entry of a light cable 36 which houses the plurality of light fibers 22. Light cable 36 runs along cable 32 to the distal end of the endoscope, or light cable 36 can join cable 32 within the channel 13 as shown in FIG. 1a. Thus cable 32 would house both the light fibers and the conductors which interconnect the control box 30 to the image sensor 40.

Image sensor 40 is illustrated as being a planar and square shaped member. However, the image sensor may be modified to be in a planar and circular shape to better fit within the channel defined by inner tube 20. Accordingly, FIG. 1b further shows an alternate shaped image sensor 40' which is round. A lens group or system 42 may be incorporated at the distal end of the endoscope in order to manipulate the image prior to it being impinged upon the array of pixels on the image sensor 40. This lens system 42 may be sealed at the distal end 16 of the endoscope so that the tubular portion 14 is impervious to fluids entering through the distal end 16. In the configuration of the imaging device 11 in FIGS. 1a and 1b, there are only three conductors which are necessary for providing power to the image sensor 40, and for transmitting an image from the image sensor 40 back to the processing circuitry found within control box 30. Namely, there is a power conductor 44, a grounding conductor 46, and an image signal conductor 48 each of which are hard wired to the image sensor. Thus, cable 26 may simply be a three-conductor 50 ohm cable.

Image sensor 40 can be as small as 1 mm in its largest dimension. However, a more preferable size for most endoscopic procedures would dictate that the image sensor 40 be between 4 mm to 8 mm in its largest dimension. The image signal electrically transmitted from the image sensor through conductor 48 is also herein referred to as a pre-video signal. Once the pre-video signal has been electrically transmitted from image sensor 40 by means of conductor 48, it is received by video processing board 50. Video processing board 50 then carries out all the necessary conditioning of the pre-video signal and places it in a form so that it may be viewed directly on a standard video device, television or standard computer video monitor. The signal produced by the video processing board 50 can be further defined as a post-video signal which can be accepted by a standard video device. As shown in FIG. 1*a*, a conductor 49 is provided which electrically transmits the post-video signal to an output connector 58 on the exterior surface of control box 30. The cable (not shown) extending from the desired video device (not shown) may receive the post-video signal by means of connector 58. Power supply board 52 may convert incoming power received through power source 54 into the desired voltage. In the preferred imager incorporated in this invention, the power to the imaging device is simply a direct current which can be a 1.5 volt to a 12 volt source. Incoming power from, for example, a wall receptacle, communicates with power supply board 52 by connector 56. Power supply board 52 takes the incoming power source and regulates it to the desired level. Additionally, ground 46 is also shown as extending back to the source of power through connector 56.

Figure 2:
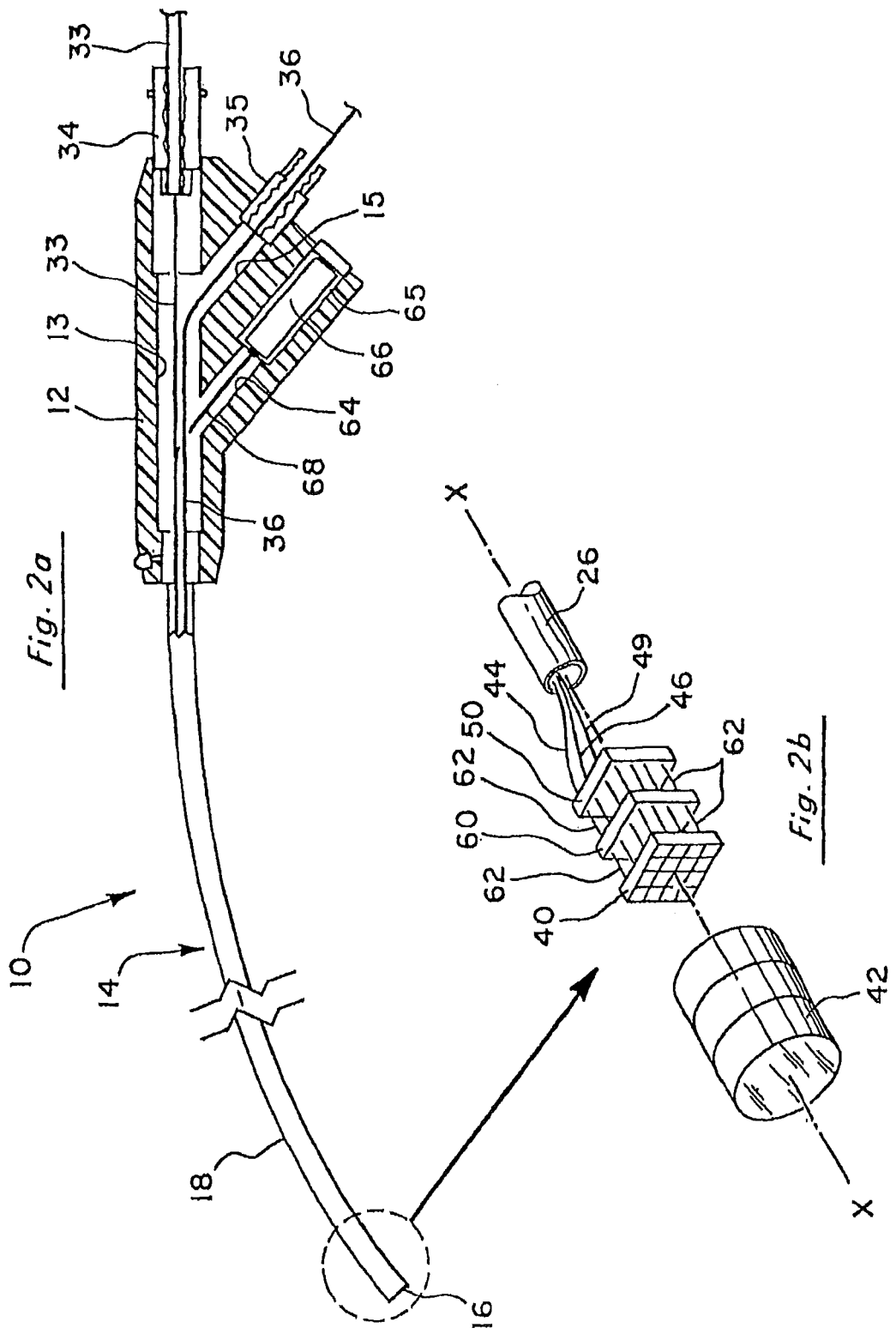
FIG. 2a is a fragmentary cross-sectional view of the endoscope in the first embodiment, and a second arrangement of the imaging device wherein the imaging device is incorporated in its entirety at the distal tip of the endoscope.
FIG. 2b is an enlarged fragmentary partially exploded perspective view of the distal end of the endoscope of FIG. 2a illustrating the imaging device.

FIG. 2*a* illustrates a second arrangement of the imaging device wherein the imaging device is self-contained entirely within the distal end 16 of the endoscope, and a power source which drives the circuitry within the imaging device may come from a battery 66 housed within handle portion 12.

As shown in FIG. 2*b*, the video processing board 50 may be placed directly behind image sensor 40. A plurality of pin connectors 62 serve to electrically couple image sensor 40 with video processing board 50 depending upon the specific configuration of image sensor 40, pin connectors 62 may be provided either for structural support only, or to provide a means by which image signals are electrically transmitted between image sensor 40 and board 50. When necessary, one or more supplementary boards 60 may be provided which further contain processing circuitry to process the image signal and present it in a form which may be directly received by a desired video device. The area which is occupied by image sensor 40 may be defined as the profile area of the imaging device and which determines its critical dimensions. Any imaging elements that are found on boards 50 or 60 must be able to be placed on one or more circuit boards which are longitudinally aligned with image sensor 40 along longitudinal axis XX. If the profile area is not critical in terms of limiting the largest sized imaging element within the imaging device, then the additional circuit boards 50 and 60 which are normally placed in line with image sensor 40 can be aligned in an offset manner or may be larger than the profile area of image sensor 40. In the configuration of FIG. 2*b*, it is desirable that elements 40, 50 and 60 be approximately the same size so that they may fit uniformly within the central channel of the endoscope. Additionally, image sensor 40 may be bonded to lens system 42 in order to provide further structural support to the imaging device 11 when mounted within the distal end 16.

Referring back to the handle portion 12 in FIG. 2*a*, an additional channel 64 may be provided in order that a power supply cable 68 may communicate with battery 66. Conveniently, battery 66 may itself be mounted within a well 65 formed in handle portion 12. Cable 68 carries the conductor 44 and ground 46. Cable 68 may intersect with cable 33 within channel 13, cables 68 and 33 extending then to the distal end 16. Cable 33 can be a single conductor cable which transmits the post-video signal to a desired video device. In other words, cable 33 may simply be an insulated and shielded housing for conductor 49 which carries the post-video signal. Because a preferred image sensor of the imaging device 11 may only require a 5 volt power supply, a battery is an ideal power source in lieu of a conductor which would trail the endoscope. Accordingly, the endoscope is made more mobile and easier to handle by eliminating at least one of the trailing cables.

FIG. 3*a* illustrates yet another arrangement or configuration of the imaging device wherein the imaging device can be used in conjunction with a standard rod lens endoscope 70. As shown, rod lens endoscope 70 includes a lens train 72 which includes a plurality of highly precise lenses (not shown) which are able to transmit an image from the distal end of the endoscope, to a camera in line with the endoscope. The rod lens endoscope is equipped with a light guide coupling post 74. Light guide post 74 connects to a source of light in the form of a cable 77 having a plurality of fiber optic strands (not shown) which communicate with a source of light (not shown). The most common arrangement of the rod lens endoscope also includes a "C" or "V" mount connector 78 which attaches to the eyepiece 76. The "C" or "V" mount attaches at its other end to a camera group 80. The camera group 80 houses one or more of the elements of the imaging device. In this configuration, the small size of the imaging device is not a critical concern since the imaging device is not being placed at the distal end of the endoscope. However, the incorporation of the imaging device in a housing which would normally hold a traditional camera still provides an advantageous arrangement. As shown, the camera group 80 may include a housing 82 which connects to a power/video cable 86. Fitting 87 is provided to couple cable 86 to the interior elements of the camera group 80 found within housing 82. FIG. 3*a* illustrates an arrangement of the imaging device 11 wherein the image sensor 40 is placed by itself within the housing 82 and the processing circuitry of the imaging device can be positioned in a remote control box as shown in FIG. 1*a*. Accordingly, only three conductors 44, 46 and 48 are necessary for providing power to the image sensor 40 and for transmitting the pre-video signal to the control box. Alternatively, as shown in FIG. 3*b*, the entire imaging device 11 may be incorporated within camera group 80, each of the elements of the imaging device being placed in the stacked arrangement similar to FIG. 2*b*. As discussed above, size is not as much of a concern in the embodiment of FIGS. 3*a* and 3*b* since the camera group housing 82 is much larger than the distal tip of the endoscope of FIGS. 1*a* and 2*a*.

FIG. 3*c* also illustrates the use of a battery 66 which provides source of power to the imaging device in either FIG. 3*a* or 3*b*. In this arrangement, housing 82 is altered to include a battery housing 69 which houses the battery 66 therein. Battery housing 69 may include a very small diameter channel which may allow conductor 48 or 49 to communicate directly with the processing circuitry or video device, respectively. It will also be understood that the embodiment in FIG. 1a may incorporate the use of a battery 66 as the source of power. Thus, handle 12 in FIG. 1a may be altered in the same way as housing 82 to allow a battery to be attached to the handle portion 12.

In all of the arrangements of the imaging device discussed above with respect to the first embodiment of the endoscope, each of the elements or components of the imaging device electrically communicate with one another through a wired connection.

Figure 4:
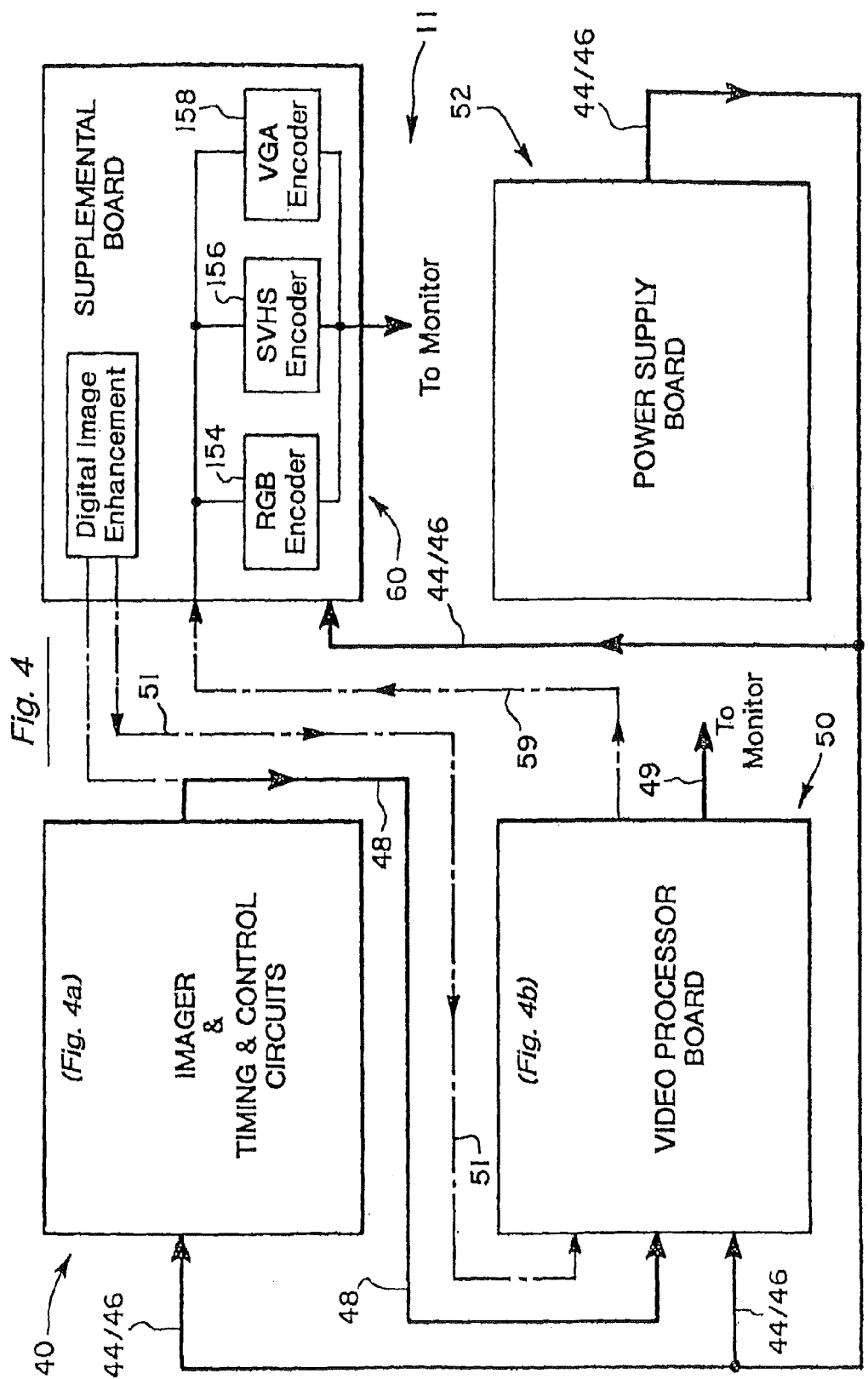
FIG. 4 is a schematic diagram of the functional electronic components which make up the imaging device.

FIG. 4 is a schematic diagram illustrating one way in which the imaging device 11 may be constructed. As illustrated, the image sensor 40 may include the timing and control circuits on the same planar structure. Power is supplied to image sensor 40 by power supply board 52. The connection between image sensor 40 and board 52 may simply be a cable having two conductors therein, one for ground and another for transmitting the desired voltage. These are illustrated as conductors 44 and 46. The output from image sensor 40 in the form of the pre-video signal is input to video processor board 50 by means of the conductor 48. In the configuration of FIG. 4, conductor 48 may simply be a 50 ohm conductor. Power and ground also are supplied to video processing board 50 by conductors 44 and 46 from power supply board 52. The output signal from the video processor board 50 is in the form of the post-video signal and which may be carried by conductor 49 which can also be a 50 ohm conductor.

In the first arrangement of the imaging device illustrated in FIG. 1a, cable 32 can be used to house conductors 44, 46 and 48. In the arrangement shown in FIG. 2a, cable 33 can be used to house conductor 49 by itself when a battery power source is used, or alternatively, cable 33 may house conductors 44, 46 and 49 if the arrangement of FIG. 2a utilizes a power source from board 52.

Optionally, a supplementary processing board 60 may be provided to further enhance the pre-video signal. As shown in FIG. 4, the supplementary board 60 may be placed such that the pre-video signal from image sensor 40 is first sent to the supplementary board and then output to the video processor board 50. In this case, the output from board 50 can be carried along conductor 51. This output can be defined as an enhanced pre-video signal. Furthermore, the post-video signal from video processor board 50 may return to the supplementary board 60 for further processing, as further discussed below. The conductor used to electrically transmit the post-video signal back to the supplementary board is shown as conductor 59. The power supply board 52 may also provide power to the supplementary board in the same manner as to image sensor 40 and board 50. That is, a simple hard-wired connection is made onto the supplementary board for the ground and voltage carrying conductors. As discussed above, image sensor 40 may be placed remotely from boards 50 and 60. Alternatively, image sensor 40, and boards 50 and 60 each may be placed within the distal end of the endoscope.

Although FIG. 4 illustrates the image sensor and the timing and control circuits being placed on the same planar structure, it is possible to separate the timing and control circuits from the pixel array and place the timing and control circuits onto video processing board 50. The advantage in placing the timing and control circuits on the same planar structure as the image sensor is that only three connections are required between image sensor 40 and the rest of the imaging device, namely, conductors 44, 46 and 48. Additionally, placing the timing and control circuits on the same planar structure with the pixel array results in the pre-video signal having less noise. Furthermore, the addition of the timing and control circuits to the same planar structure carrying the image sensor only adds a negligible amount of size to one dimension of the planar structure. If the pixel array is to be the only element on the planar structure, then additional connections must be made between the planar structure and the video processing board 50 in order to transmit the clock signals and other control signals to the pixel array. For example, a ribbon-type cable (not shown) or a plurality of 50 ohm coaxial cables (not shown) must be used in order to control the downloading of information from the pixel array. Each of these additional connections would be hard wired between the boards.

Figure 3:
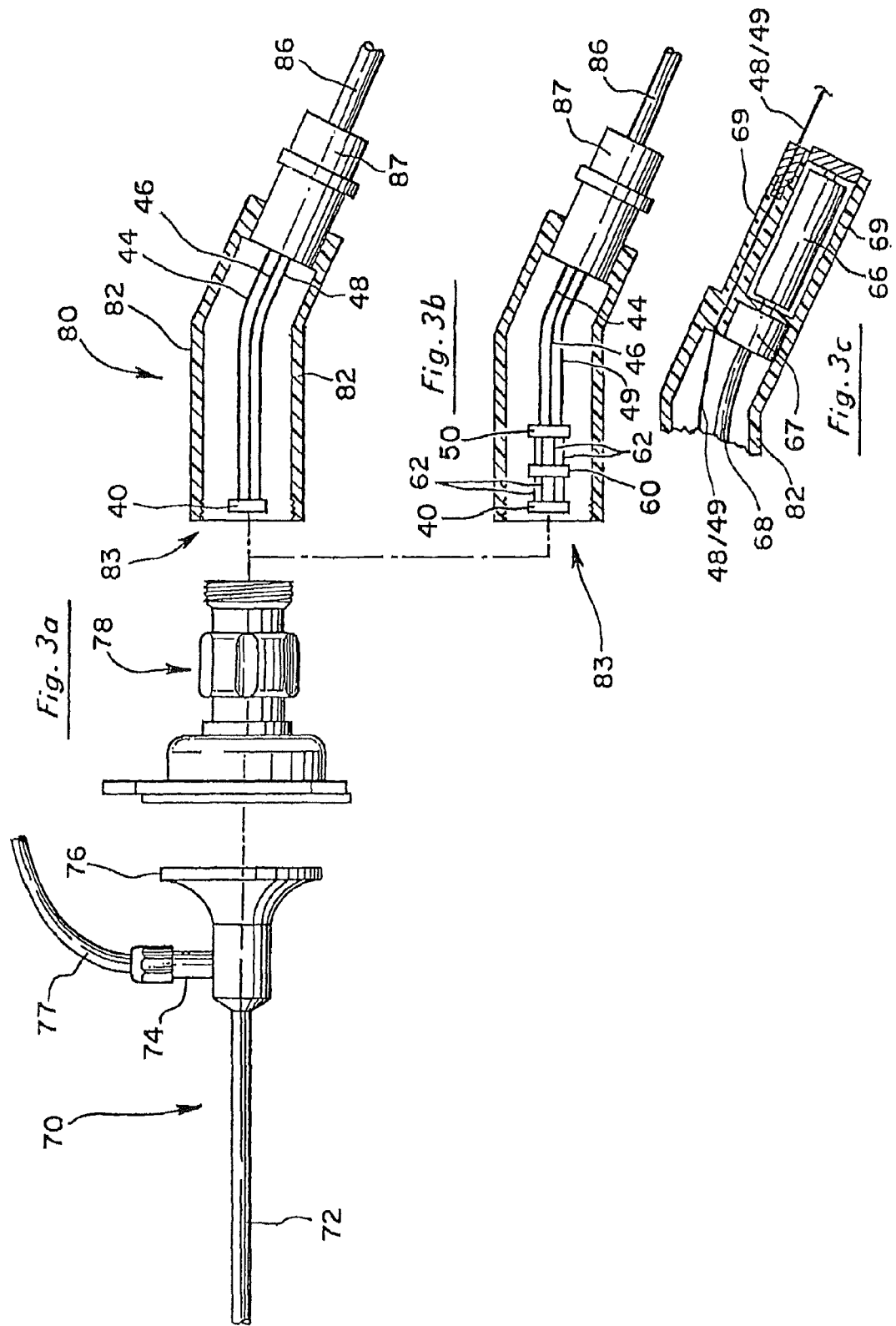
Figure 4A:
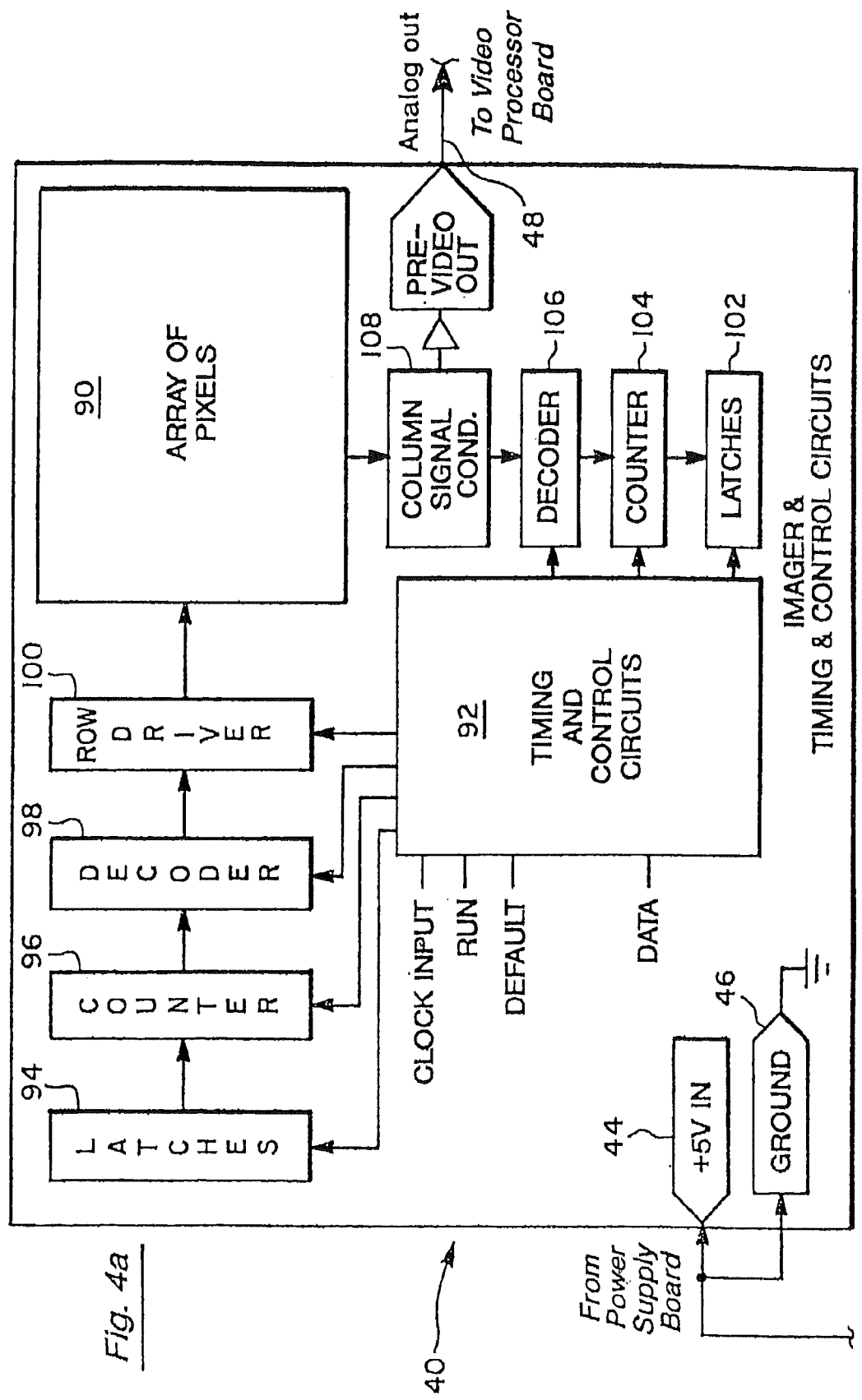
FIG. 4a is an enlarged schematic diagram of a circuit board which may include the array of pixels and the timing and control circuitry.

FIG. 4a is a more detailed schematic diagram of image sensor 40 which contains an array of pixels 90 and the timing and control circuits 92. One example of a pixel array 90 which can be used within the invention is similar to that which is disclosed in U.S. Pat. No. 5,471,515 to Fossum, et al., said patent being incorporated by reference herein. More specifically, FIG. 3 of Fossum, et al. illustrates the circuitry which makes up each pixel in the array of pixels 90. The array of pixels 90 as described in Fossum, et al. is an active pixel group with intra-pixel charged transfer. The image sensor made by the array of pixels is formed as a monolithic complementary metal oxide semiconductor integrated circuit which may be manufactured in an industry standard complementary metal oxide semiconductor process. The integrated circuit includes a focal plane array of pixel cells, each one of the cells including a photo gate overlying the substrate for accumulating the photo generated charges. In broader terms, as well understood by those skilled in the art, an image impinges upon the array of pixels, the image being in the form of photons which strike the photo diodes in the array of pixels. The photo diodes or photo detectors convert the photons into electrical energy or electrons which are stored in capacitors found in each pixel circuit. Each pixel circuit has its own amplifier which is controlled by the timing and control circuitry discussed below. The information or electrons stored in the capacitors is unloaded in the desired sequence and at a desired frequency, and then sent to the video processing board 50 for further processing.

Although the active pixel array disclosed in U.S. Pat. No. 5,471,515 is mentioned herein, it will be understood that the hybrid CCD/CMOS described above, or any other solid state imaging device may be used wherein timing and control circuits can be placed either on the same planar structure with the pixel array, or may be separated and placed remotely. Furthermore, it will be clearly understood that the invention claimed herein is not specifically limited to an image sensor as disclosed in the U.S. Pat. No. 5,471,515, but encompasses any image sensor which may be configured for use in conjunction with the other processing circuitry which makes up the imaging device of this invention.

The timing and control circuits 92 are used to control the release of the image information or image signal stored in the pixel array. In the image sensor of Fossum, et al., the pixels are arranged in a plurality of rows and columns. The image information from each of the pixels is first consolidated in a row by row fashion, and is then downloaded from one or more columns which contain the consolidated information from the rows. As shown in FIG. 4a, the control of information consolidated from the rows is achieved by latches 94, counter 96, and decoder 98. The operation of the latches, counter and decoder is similar to the operation of similar control circuitry found in other imaging devices. That is, a latch is a means of controlling the flow of electrons from each individual addressed pixel in the array of pixels. When a latch 94 is enabled, it will allow the transfer of electrons to the decoder 98. The counter 96 is programmed to count a discrete amount of information based upon a clock input from the timing and control circuits 92. When the counter 96 has reached its set point or overflows, the image information is allowed to pass through the latches 94 and be sent to the decoder 98 which places the consolidated information in a serial format. Once the decoder 98 has decoded the information and placed it in the serial format, then the row driver 100 accounts for the serial information from each row and enables each row to be downloaded by the column or columns. In short, the latches 94 will initially allow the information stored in each pixel to be accessed. The counter 96 then controls the amount of information flow based upon a desired time sequence. Once the counter has reached its set point, the decoder 98 then knows to take the information and place it in the serial format. The whole process is repeated, based upon the timing sequence that is programmed. When the row driver 100 has accounted for each of the rows, the row driver reads out each of the rows at the desired video rate.

The information released from the column or columns is also controlled by a series of latches 102, a counter 104 and a decoder 106. As with the information from the rows, the column information is also placed in a serial format which may then be sent to the video processing board 50. This serial format of column information is the pre-video signal carried by conductor 48. The column signal conditioner 108 places the column serial information in a manageable format in the form of desired voltage levels. In other words, the column signal conditioner 108 only accepts desired voltages from the downloaded column(s).

The clock input to the timing and control circuits 92 may simply be a quartz crystal timer. This clock input is divided into many other frequencies for use by the various counters. The run input to the timing and control circuit 92 may simply be an on/off control. The default input can allow one to input the pre-video signal to a video processor board which may run at a frequency of other than 30 hertz. The data input controls functions such as zoom. At least for a CMOS type active pixel array which can be accessed in a random manner, features such as zoom are easily manipulated by addressing only those pixels which locate a desired area of interest by the surgeon.

A further discussion of the timing and control circuitry which may be used in conjunction with an active pixel array is disclosed in U.S. Pat. No. 5,471,515 and is also described in an article entitled "Active Pixel Image Sensor Integrated With Readout Circuits" appearing in *NASA Tech Briefs*, October 1996, pp. 38 and 39. This particular article is also incorporated by reference.

Figure 4B:
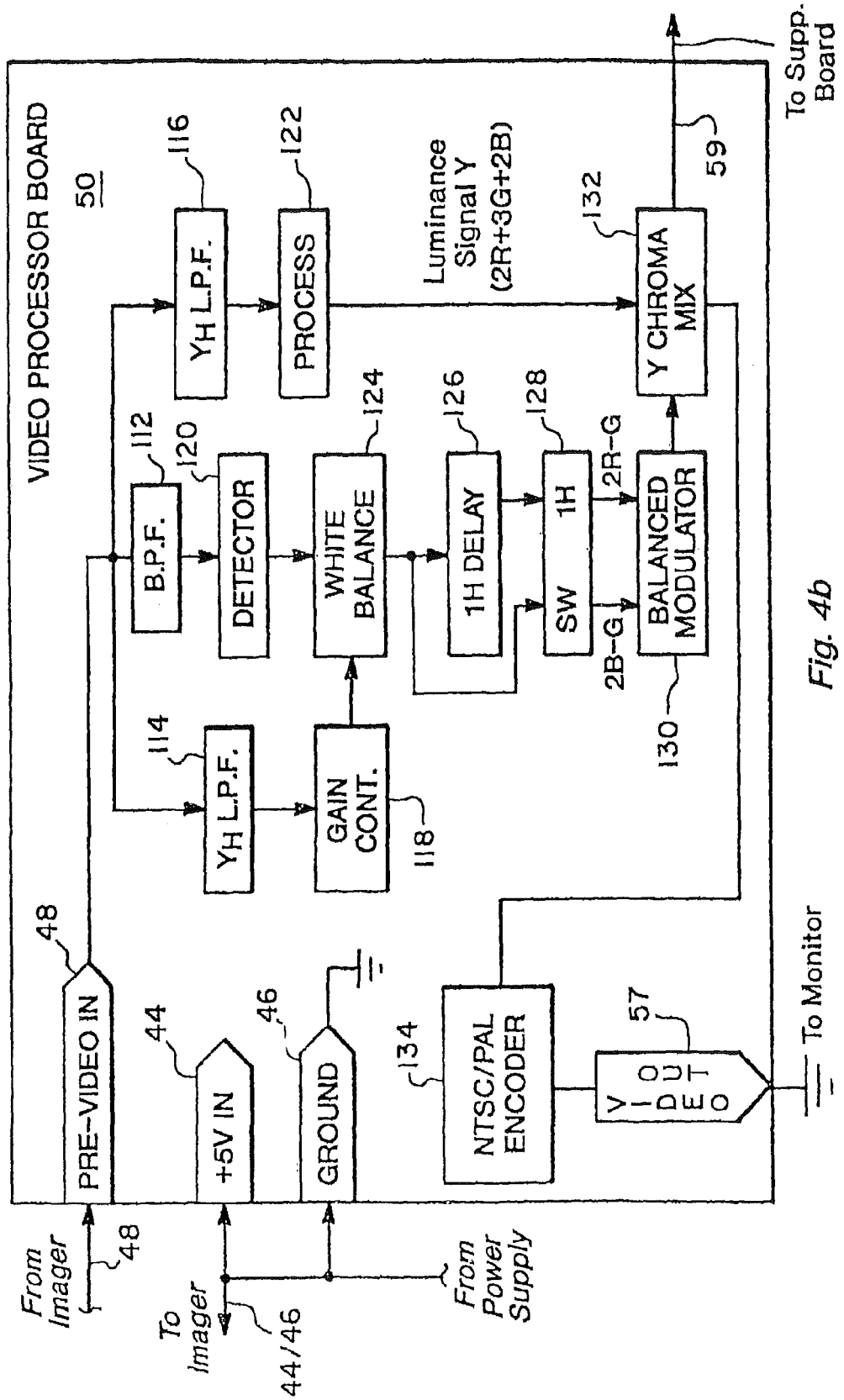
FIG. 4b is an enlarged schematic diagram of a video processing board having placed thereon the processing circuitry which processes the pre-video signal generated by the array of pixels and which converts the pre-video signal to a post-video signal which may be accepted by a standard video device.

Once image sensor 40 has created the pre-video signal, it is sent to the video processing board 50 for further processing. At board 50, as shown in FIG. 4b, the pre-video signal is passed through a series of filters. One common filter arrangement may include two low pass filters 114 and 116, and a band pass filter 112. The band pass filter only passes low frequency components of the signal. Once these low frequency components pass, they are then sent to detector 120 and white balance circuit 124, the white balance circuit distinguishing between the colors of red and blue. The white balance circuit helps the imaging device set its normal, which is white. The portion of the signal passing through low pass filter 114 then travels through gain control 118 which reduces the magnitude or amplitude of this portion to a manageable level. The output from gain control 118 is then fed back to the white balance circuit 124. The portion of the signal traveling through filter 116 is placed through the processor 122. In the processor 122, the portion of the signal carrying the luminance or non-chroma is separated and sent to the Y chroma mixer 132. Any chroma portion of the signal is held in processor 122.

Referring to the output of the white balance circuit 124, this chroma portion of the signal is sent to a delay line 126 where the signal is then further reduced by switch 128. The output of switch 128 is sent through a balanced modulator 130 and also to the Y chroma mixer 132 where the processed chroma portion of the signal is mixed with the processed non-chroma portion. Finally, the output from the Y chroma mixer 132 is sent to the NTSC/PAL encoder 134, commonly known in the art as a "composite" encoder. The composite frequencies are added to the signal leaving the Y chroma mixer 132 in encoder 134 to produce the post-video signal which may be accepted by a television or other video display device.

Referring back to FIG. 4, it further illustrates supplementary board 60 which may be used to digitally enhance or otherwise further condition the pre-video signal produced from image sensor 40. For example, digital enhancement can brighten or otherwise clarify the edges of an image viewed on a video screen. Additionally, the background images may be removed thus leaving only the foreground images or vice versa. The connection between image sensor 40 and board 60 may simply be the conductor 48 which may also transfer the pre-video signal to board 50. Once the pre-video signal has been digitally enhanced on supplementary board 60, it is then sent to the video processor board 50 by means of another conductor 51. The pre-video signal is an analog signal. The digitally enhanced pre-video signal may either be a digital signal or it may be converted back to the analog domain prior to being sent to board 50.

In addition to digital enhancement, supplementary board 60 may further include other circuitry which may further condition the post-video signal so that it may be viewed in a desired format other than NTSC/PAL. As shown in FIG. 4, intermediate conductor 59 may transmit the signal output from Y chroma mixer 132 back to the supplementary board 60 where the signal is further encoded for viewing in a particular format. One common encoder which can be used includes an RGB encoder 154. The RGB encoder separates the signal into three separate colors (red, green and blue) so that the surgeon may selectively choose to view only those images containing one or more of the colors. Particularly in tissue analysis where dyes are used to color the tissue, the RGB encoder may help the surgeon to identify targeted tissue.

The next encoder illustrated in FIG. 4 is a SVHS encoder 156 (super video home system). This encoder splits or separates the luminance portion of the signal and the chroma portion of the signal prior to entering the video device. Some observers believe that a cleaner signal is input to the video device by such a separation which in turn results in a more clear video image viewed on the video device. The last encoder illustrated in FIG. 4 is a VGA encoder 158 which enables the signal to be viewed on a standard VGA monitor which is common to many computer monitors.

One difference between the arrangement of image sensor 40 and the outputs found in FIG. 3 of the Fossum, et al. patent is that in lieu of providing two analog outputs [namely, VS out (signal) and VR out (reset)], the reset function takes place in the timing and control circuitry 92. Accordingly, the pre-video signal only requires one conductor 48.

FIGS. 5a-5e illustrate in more detail one example of circuitry which may be used in the video processing board 50 in order to produce a post-video signal which may be directly accepted by a video device such as a television. The circuitry disclosed in FIGS. 5a-5e is very similar to circuitry which is found in a miniature quarter-inch Panasonic camera, Model KS-162. It will be understood by those skilled in the art that the particular arrangement of elements found in FIGS. 5a-5e are only exemplary of the type of video processing circuitry which may be incorporated in order to take the pre-video signal and condition it to be received by a desired video device.

Figure 5A:
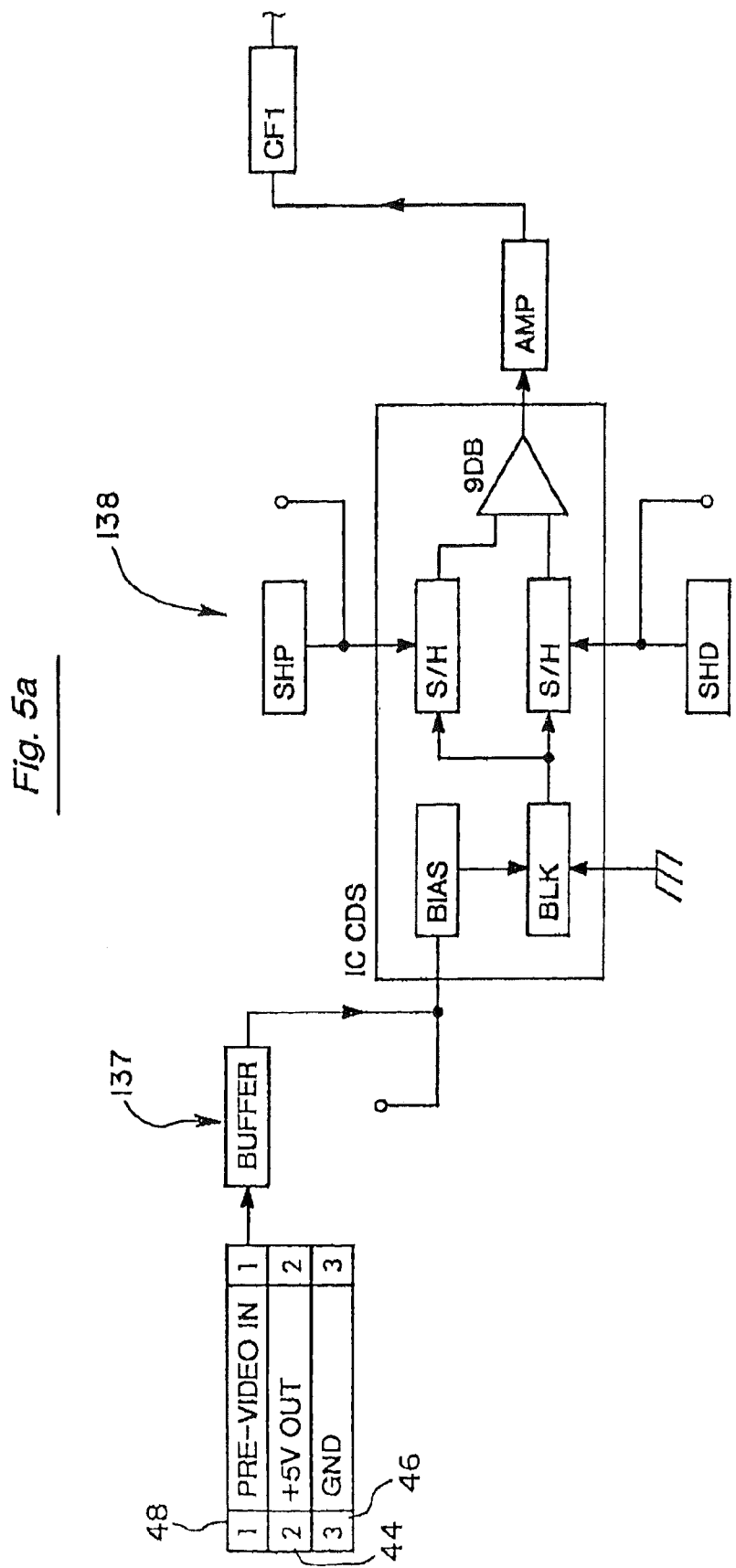
FIGS. 5a-5e are schematic diagrams that illustrate an example of specific circuitry which may be used to make the imaging device.

As shown in FIG. 5a, 5 volt power is provided along with a ground by conductors 44 and 46 to board 50. The pre-video signal carried by conductor 48 is buffered at buffer 137 and then is transferred to amplifying group 138. Amplifying group 138 amplifies the signal to a usable level as well as achieving impedance matching for the remaining circuitry.

Figure 5B:
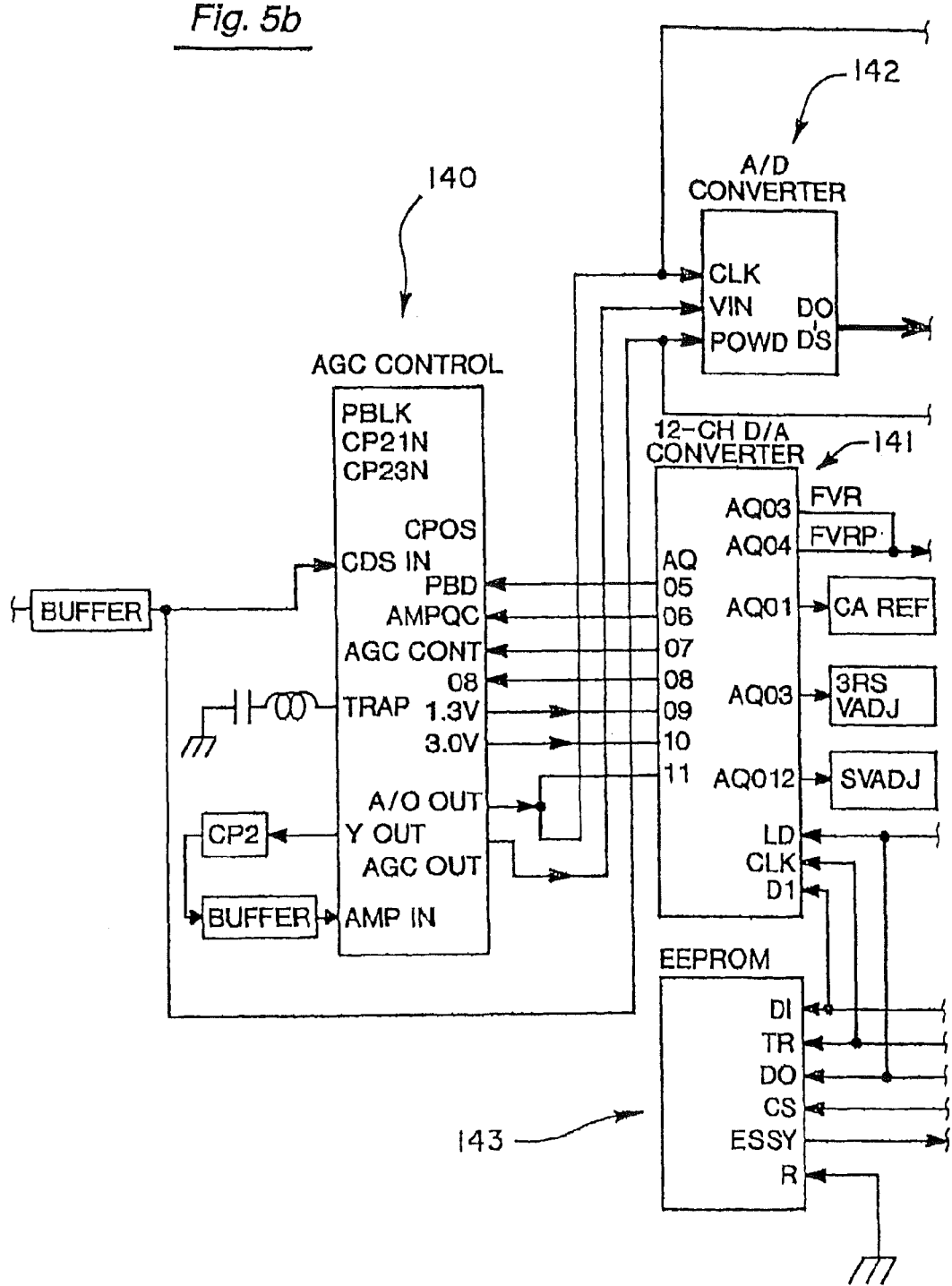

The next major element is the automatic gain control 140 shown in FIG. 5b. Automatic gain control 140 automatically controls the signal from amplifying group 138 to an acceptable level and also adds other characteristics to the signal as discussed below. More specifically, automatic gain control 140 conditions the signal based upon inputs from a 12 channel digital to analog converter 141. Converter 141 retrieves stored information from EEPROM (electrically erasable programmable read only memory) 143. EEPROM 143 is a non-volatile memory element which may store user information, for example, settings for color, tint, balance and the like. Thus, automatic gain control 140 changes the texture or visual characteristics based upon user inputs. The signal leaving the automatic gain control 140 is an analog signal until being converted by analog to digital converter 142.

Figure 5C:
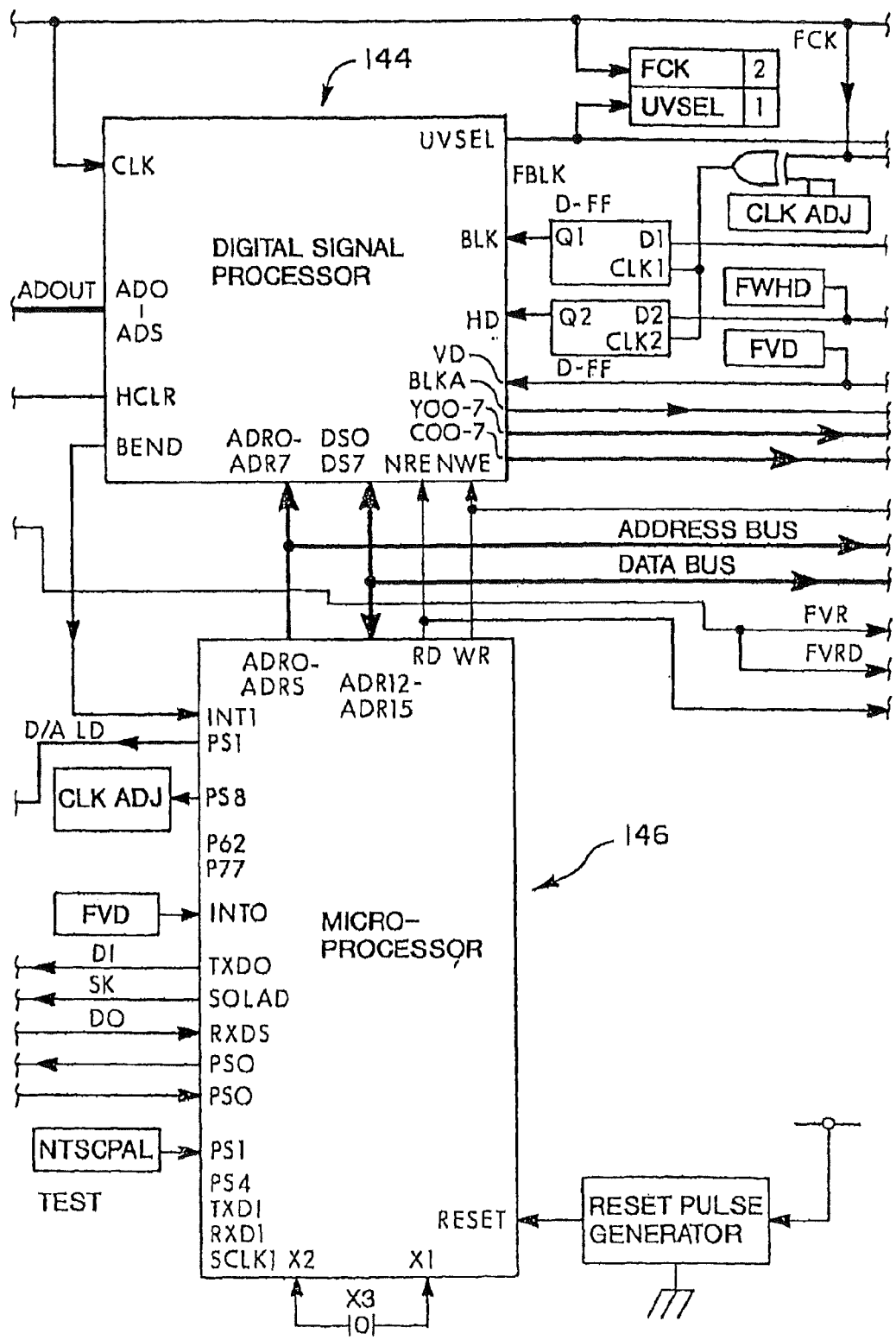

Digital signal processor 144 of FIG. 5c further processes the converted signal into a serial type digital signal. One function of the microprocessor 146 is to control the manner in which digital signal processor 144 sorts the digital signals emanating from converter 142. Microprocessor 146 also controls analog to digital converter 142 in terms of when it is activated, when it accepts data, when to release data, and the rate at which data should be released. Microprocessor 146 may also control other functions of the imaging device such as white balance. The microprocessor 146 may selectively receive the information stored in the EEPROM 143 and carry out its various commands to further control the other elements within the circuitry.

Figure 5D:
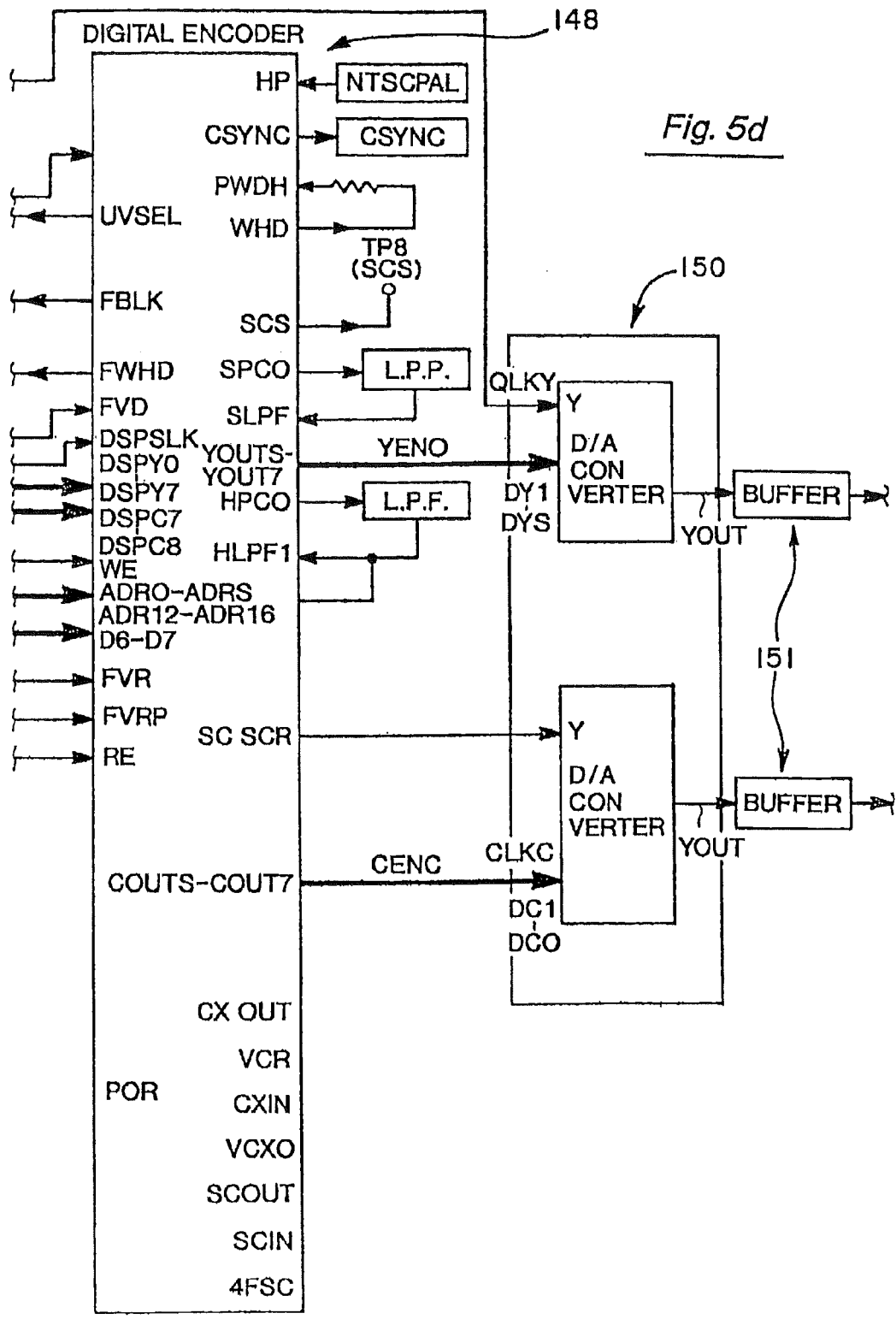

After the signal is processed by digital signal processor 144, the signal is sent to digital encoder 148 illustrated in FIG. 5d. Some of the more important functions of digital encoder 148 are to encode the digital signal with synchronization, modulated chroma, blanking, horizontal drive, and the other components necessary so that the signal may be placed in a condition for reception by a video device such as a television monitor. As also illustrated in FIG. 5d, once the signal has passed through digital encoder 148, the signal is reconverted into an analog signal through digital to analog converter 150.

Figure 5E:
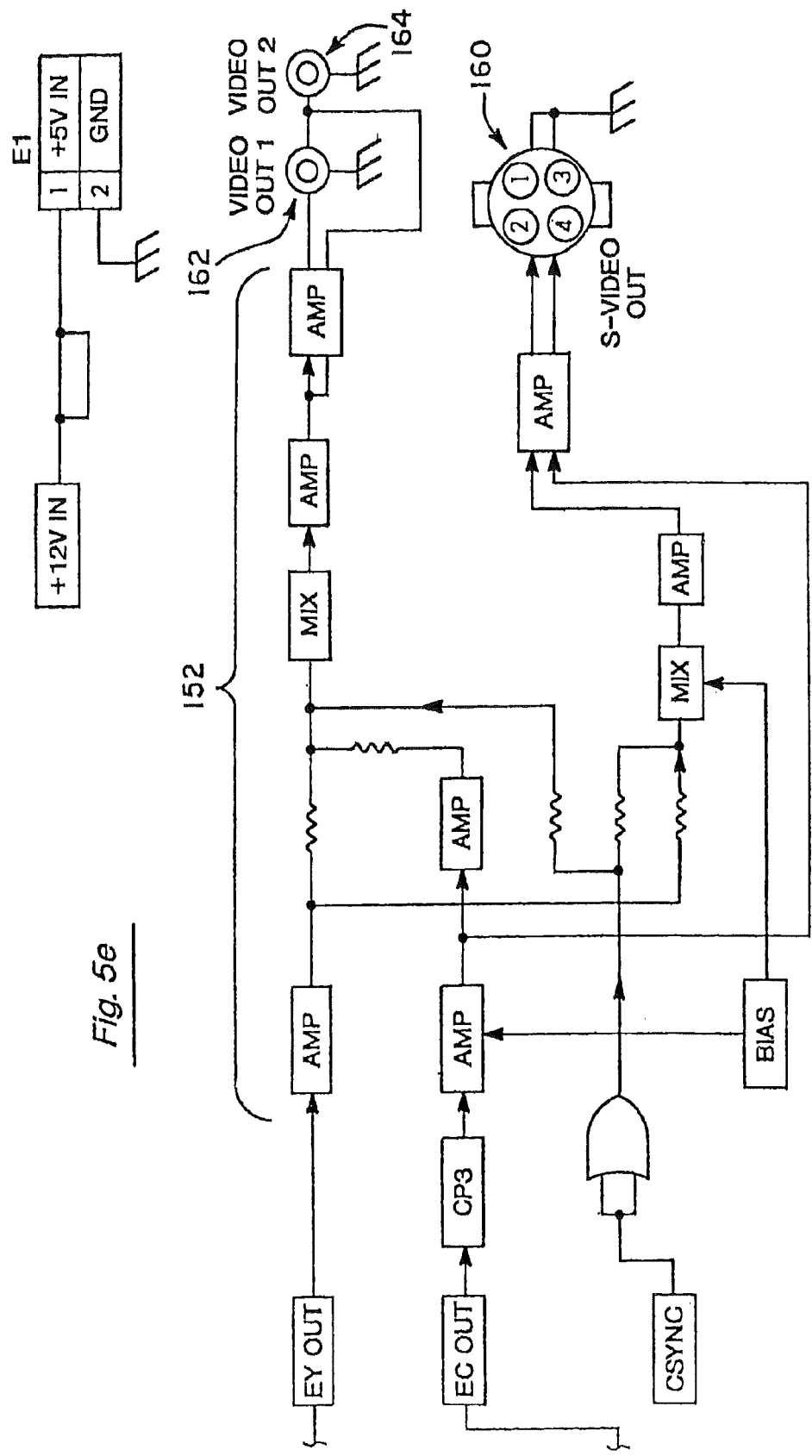

This reconverted analog signal is then buffered at buffers 151 and then sent to amplifier group 152 of FIG. 5e which amplifies the signal so that it is readily accepted by a desired video device. Specifically, as shown in FIG. 5e, one SVHS outlet is provided at 160, and two composite or NTSC outlets are provided at 162 and 164, respectively.

Now turning to a discussion of the endoscope of the second embodiment, attention is first directed to FIG. 6. In this second embodiment, like reference numerals denote matching elements from the endoscope of the first embodiment. The endoscope of the second embodiment also can be characterized as a common or generic endoscope except for the imaging device and the wireless communications means incorporated in this second embodiment. FIG. 6 more specifically illustrates the arrangement of the imaging device wherein processing of the image signals is conducted within the endoscope such that a post-video signal is ready for transmission to a display monitor. As shown, video processing board 50 is mounted adjacent the image sensor 40 in the distal tip of the endoscope. As discussed above, one or more supplementary boards 60 may also be mounted adjacent the video processing board 50 for further processing of the image signals to produce a post-video signal of a desired format. Alternatively, and as further discussed below, some or all of the processing circuitry may be mounted within the handle 12, in a specified portion of the channel 13. There is ample room within channel 13, or some other bore which could be formed in the handle to receive processing circuitry. The construction of the distal tip of the endoscope in the second embodiment can be the same as in the first embodiment. Thus, steering wires (not shown) and circumferentially spaced light fibers (not shown) may be incorporated in the endoscope. Cable 32 carrying the post-video signals electrically connects to a transceiver radio element 170 which is housed within channel 13 towards the proximal end of the handle 12. Transceiver radio element 170 conditions the post video signals in accordance with the desired wireless standard. More specifically, the transceiver radio element adds a high frequency carrier signal and baseband protocol to the post video signals, and then wirelessly transmits the post video signals via antennae 174 to the transceiver radio module 178. The transceiver radio module 178 authenticates the received signals, strips the signals of the carrier frequency, and then routs the signals in the final video format to a display monitor 196. It should also be understand that the communications between the transceiver radio element 170 and the transceiver radio module 178 are not simply one-way communications; rather, the communications are two way in accordance with the Bluetooth standard or IEEE standard. For example, not only does the transceiver radio element 170 transmit image signals, but the transceiver radio element 170 also receives and processes authentication signals from the radio transceiver module 178. Similarly, not only does the transceiver radio module 178 receive and process image signals, but the module 178 also transmits authentication signals. A power switch (not shown) may also be incorporated within the endoscope to selectively energize or de-energize the image sensor 40 and the transceiver radio element 170.

Transceiver radio module 178 receives the post-video signals via antennae 180, decodes the signals, and then electrically transmits them to the monitor 196 for viewing by the user. The endoscope in this second embodiment is powered by a battery 176 which is housed adjacent the antennae 174. Electrical leads (not shown) extend from the battery 176 to power the image sensor and the transceiver radio element 170. As discussed further below, antennae 174 and battery 176 may be secured within their own casing or housing 172 which then connects to the handle 12 of the endoscope. Transceiver radio module 178 may simply be powered by the same electrical power source (not shown) which powers the display monitor 196, such as conventional 110 volt, 3 phase power. In order to recharge the battery 176 of the endoscope, the transceiver radio module may be a combination unit which also has a battery charge circuit 182 for recharging battery 176. Charge circuit 182 would also be powered by a conventional power source, preferably the same power source powering the transceiver module 178 and the display monitor 196. Circuit 182 would have a charging receptacle, shown schematically as receptacle 186, for receiving the battery 176. FIG. 6 also shows a self-contained white light source in the form of light source 192 which is housed in channel 15 between interior plug 194 and exterior plug or access cover 195. Alternatively, as shown in FIG. 6a, an exterior source of light 198 could be used which transmits light through the cable 36. The self contained light source 192 is preferred because the endoscope is then free from all trailing cables or other wiring.

FIG. 6b illustrates the endoscope having another cavity or opening 210 formed therein for housing some or all of the processing circuitry. As shown, the video processor board 50 has been moved to the opening 210 and is supported in the opening by support 212 which is placed in the opening 210 at a selected depth to accommodate the particular sized circuitry placed in the opening. Conductor 214 interconnects the board 50 with image sensor 40, and conductor 214 can run coterminously with cable 32. Accordingly, the only imaging device element remaining in the distal end of the endoscope is the image sensor 40. Additionally, the timing and control circuits 92 could also be placed in the opening 210 along with the video processing circuitry. The co-pending application Ser. No. 09/368,246 is also incorporated herein by reference for purposes of disclosing circuitry placed in the handle of the endoscope.

FIGS. 8 and 9 illustrate another arrangement of the imaging device incorporated within the endoscope of the second embodiment. In preface, FIGS. 8 and 9 illustrate the arrangement in which some elements of the imaging device are placed within the endoscope, and remaining elements of the imaging device are placed within the control box 30. Wireless transmission of image signals takes place between the endoscope and the control box. Final transmission of the post-video signal can then be conducted either electrically through a cable interconnecting the display monitor and the control box, or final transmission may take place via another wireless transmission of the post-video signal from the control box to the display monitor.

Referring first to FIG. 8, the endoscope is shown which is identical to the endoscope shown in FIG. 6 with the exception that there is no video processor board 50 or other associated video processing circuitry housed within the endoscope. Thus, the transceiver radio element 170 receives a pre-video signal form the image sensor 40, and then wirelessly transmits the pre-video signal to the control box 30. The transceiver radio module 178 receives the pre-video signal and transfers the same to video processor board 50. Video processor board 50 alone or in conjunction with other processing circuitry such as a supplementary processing board 60 (not shown) places the image signal in a post-video format for direct reception by the display monitor 196. Additionally, it is also contemplated that the timing and control circuitry 92 could be placed in the control box 30. In such a case, the transceiver radio module 178 would not only transmit authentication signals, but also signals generated from the timing and control circuitry 92 for controlling the image sensor 40.

In lieu of a camera battery charge circuit incorporated within a unit which is co-located with the display monitor as shown in FIG. 7, the charge circuit 182 may be housed within the control box 30. Accordingly, circuit 182 could be powered by power supply board 52. Additionally, a camera power switch 184 could be included within control box 30 to selectively energize or de-energize the video processor board and its function in converting pre-video signals to post-video signals. As in the endoscope of FIG. 6, the endoscope of FIG. 8 could also have its own power switch (not shown) to energize or de-energize functioning of the imaging elements and the transceiver radio module 170.

FIG. 9 also illustrates a secondary communications scheme whereby the post video signals could be wirelessly transmitted to the display monitor 196. Optionally, video processor board 50 (or other processing circuitry) could electrically communicate with a secondary RF transmitter 200 which would transmit the post-video signals via antennae 202. These post-video signals would then be received via antennae 206 by a secondary RF receiver 204 mounted adjacent the display monitor 196. For this secondary transmission, Bluetooth could be used; however, it would be preferable to use a different transmission standard between the primary and the secondary communications to prevent potential interference. One example of a secondary RF transmitter which could be used is an rf-video transmitter model no. SDX-22, manufactured by RF-Video.com of Toronto, Canada. This type of transmitter also operates in the 2.4 GHz frequency, and provides 80 mW of RF power. An example of an acceptable secondary RF receiver which could be used is an rf-video receiver model no. VRX-24 also manufactured by RF-Video.com. This type of receiver has an adjustable frequency of 2.2 to 2.7 Ghz.

FIG. 8a illustrates that the battery 176 may be removed from the endoscope for recharge. As shown, housing 172 carries both the antennae 174 and the battery 176; however, it shall be understood that the housing 176 could alternatively only carry the battery 176, while the antennae 174 could be housed within channel 13 of the endoscope. One practical reason for placing antennae 174 within housing 172 is that the antennae is more easily replaced if it is located within a removable element. The distal end of the housing 172 is received within well or bore 208 in the endoscope. Well 208 could be threaded to match external threads on the distal end of the housing 172, or other means such as a clip or a friction fit could be used as understood by those skilled in the art in order to connect housing 172 to the endoscope. Similarly, the proximal end of the housing 172 could be threaded or otherwise adapted so that the proximal end of the housing 172 could be received by receptacle 186 for recharge of the battery 176. As yet another option for recharge of the battery 176, a recharge cable 188 including respective fittings/connectors 190 at each end of the cable 188 could be used to interconnect battery 176 with receptacle 186. Thus if cable 188 were used, housing 172 could remain attached to the endoscope. One situation which might lend itself for use of cable 188 would be if battery 176 became discharged to the point where it failed or was in danger of failing to provide enough potential to the image sensor and transceiver radio element during a surgical procedure. Cable 188 could then be used to provide instantaneous power to the endoscope.

Figure 10:
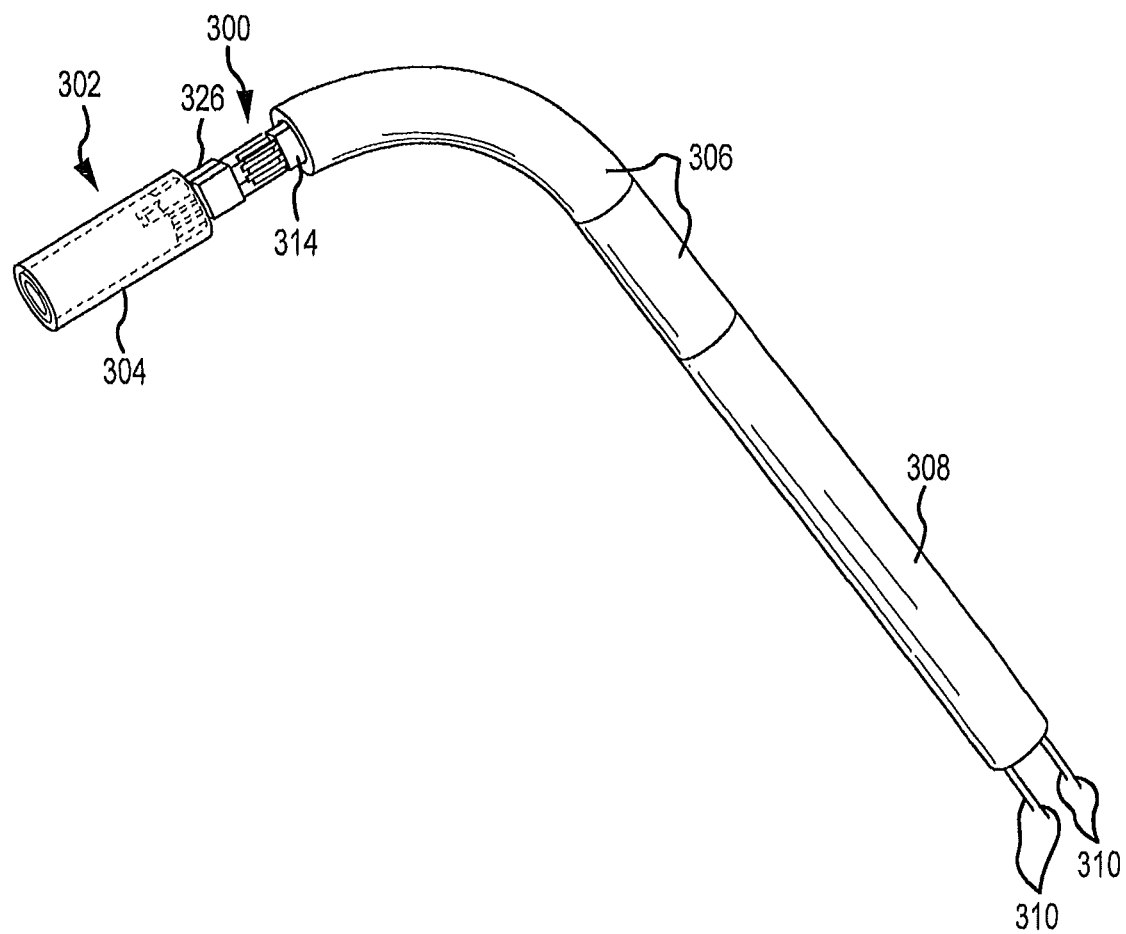
FIG. 10 is a partially exploded fragmentary perspective view of an endoscopic instrument incorporating the imaging device of the present invention, along with a connector assembly to facilitate steering of the instrument.
Figure 11:
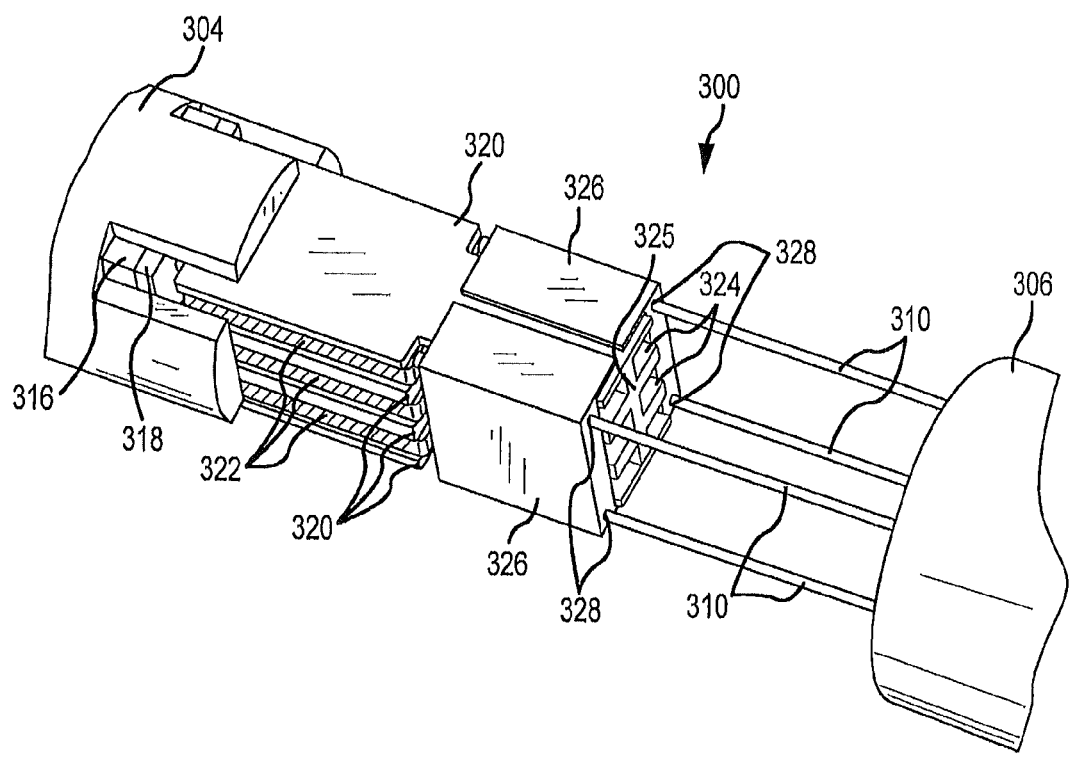
FIG. 11 is a greatly enlarged fragmentary perspective view of FIG. 10 showing further details of the connector assembly.
Figure 12:
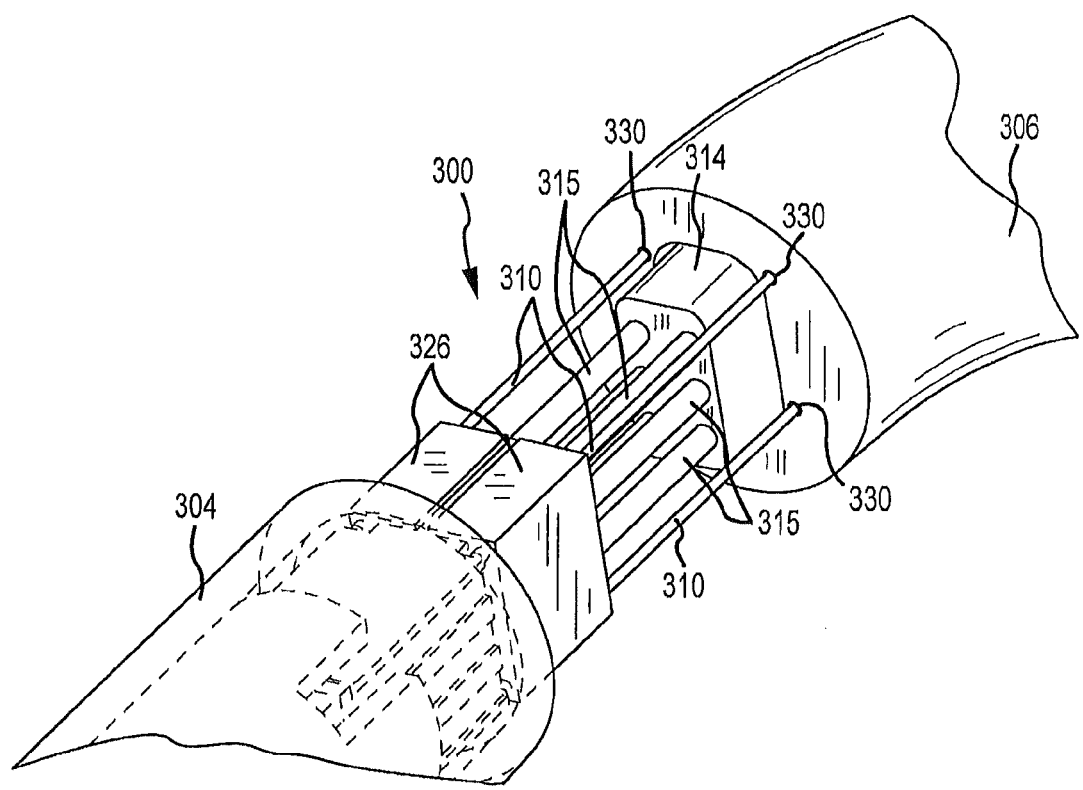
FIG. 12 is another greatly enlarged fragmentary perspective view illustrating details of the connector assembly.

Referring to FIGS. 10-12, in another aspect of the present invention, a steering connector assembly is provided in combination with the imaging device to provide a steering capability for the endoscope without increasing the size of the profile for the endoscopic device. One common prior art method of incorporating a steering capability involves the use of externally mounted steering wires and a yoke or bracket that is fitted over the distal end of the endoscope. The use of an externally mounted steering device greatly enlarges the front profile of the endoscope, and thereby prevents use of the endoscope in small passages or cavities within the body. Additionally, externally mounted steering devices can complicate overall maneuverability of the endoscope by further limiting the flexibility of the endoscope. The connector assembly of the present invention provides a fully contained or internally isolated steering capability that avoids these disadvantages of the prior art. Referring to the FIGS. 10-12, an endoscopic device is illustrated including a steering connector assembly 300 that interconnects a CMOS camera module 302 with the body of the endoscopic device. A polymer jacket 304 houses the camera elements shown in phantom lines. The endoscopic device includes one or more flexible distal body portions 306 that may articulate or bend based upon control of the steering wires 310 that extend through passages formed in the sheath of the endoscope. Preferably, the steering wires 310 run through the jacket or sheath of the endoscopic device from the proximal end as shown in FIG. 10 to the distal end as shown in FIGS. 11 and 12. The endoscopic device may also include a more rigid proximal body portion 308 that connects to a steering assembly 340 as shown in FIG. 13.

Referring to FIG. 11, details of the steering connector assembly 300 are shown. The connector assembly includes a connector body or base 320 that may be a molded piece characterized by a plurality of transverse or laterally extending flanges 324 interconnected by an orthogonally extending center member 325. The connector body 320 provides gaps or spaces in which electrical traces 322 may be housed. The electrical traces 322 electrically interconnect the CMOS imager 316 to the electrical wires 315 of the image/power cable 314, as also shown in FIG. 12. The distal end of the connector body 320 includes an imager support base 318 that is used to mount the CMOS imager 316. The electrical traces 322 therefore also extend through the mount 318 and connect to the various electrical pins or connections (not shown) of the imager 316. The proximal end of the body 320 has a smaller width dimension defined by a pair of cutouts or notches formed on opposite lateral sides of the proximal end. A strain relief member or cap 326 is mounted over the proximal end of the body 320 at the location of the notches. The strain relief member 326 serves to protect the electrical traces 322, and also serves as the anchoring point for the distal ends of the steering wires 310. As shown, the strain relief member 326 may be two channel shaped elements that attach to the opposite lateral sides of the body 320 at its proximal end. The exterior lateral edges of the member 326 are substantially planer with the exterior lateral edges of the distal end of the body 320. As illustrated, the distal ends 328 of the steering wires 310 may be embedded within the facing surface of the strain relief member 326, and the steering wires then extend proximally through the sheath of the distal body portion 306 of the endoscopic device. As illustrated, four steering wires are arranged in a rectangular arrangement and located at corners of the rectangular arrangement. The strain relief member 326 as mounted results in a frontal profile for the connector assembly 300 that does not extend beyond the frontal profile of the imaging device or the capsule 302. As shown in FIG. 11, the upper surface of the strain relief member 326 is mounted over the upper surface of the body 320, and this arrangement is also repeated with respect to the lower surface of the member 326. Therefore, the strain relief member extends slightly beyond the upper and lower surfaces of the body 320. The imaging device 316 has a slightly larger frontal profile than that of the distal end of the body 320, so the strain relief member can be incorporated to not extend beyond the profile of the imaging device since the thickness of the strain relief elements are very small. Therefore, the strain relief member fits easily within the jacket 304 of the capsule 302 and the capsule size does not have to be enlarged.

Also referring to FIG. 12, in the reverse perspective view, a plurality of openings 330 can be seen that are formed through the sheath to receive the steering wires 310. The image/power cable 314 is also illustrated that houses the plurality of wires 315. These wires 315 carry the power and electronic signals to and from the CMOS imager. For clarity, FIG. 11 does not show the electrical cable 314 and wires 315. In use, the distal ends of the wires 315 (not shown) are anchored in the gaps between the flanges 324, and these wires make contact with the electrical traces 322 that also extend through the gaps 324.

Figure 13:
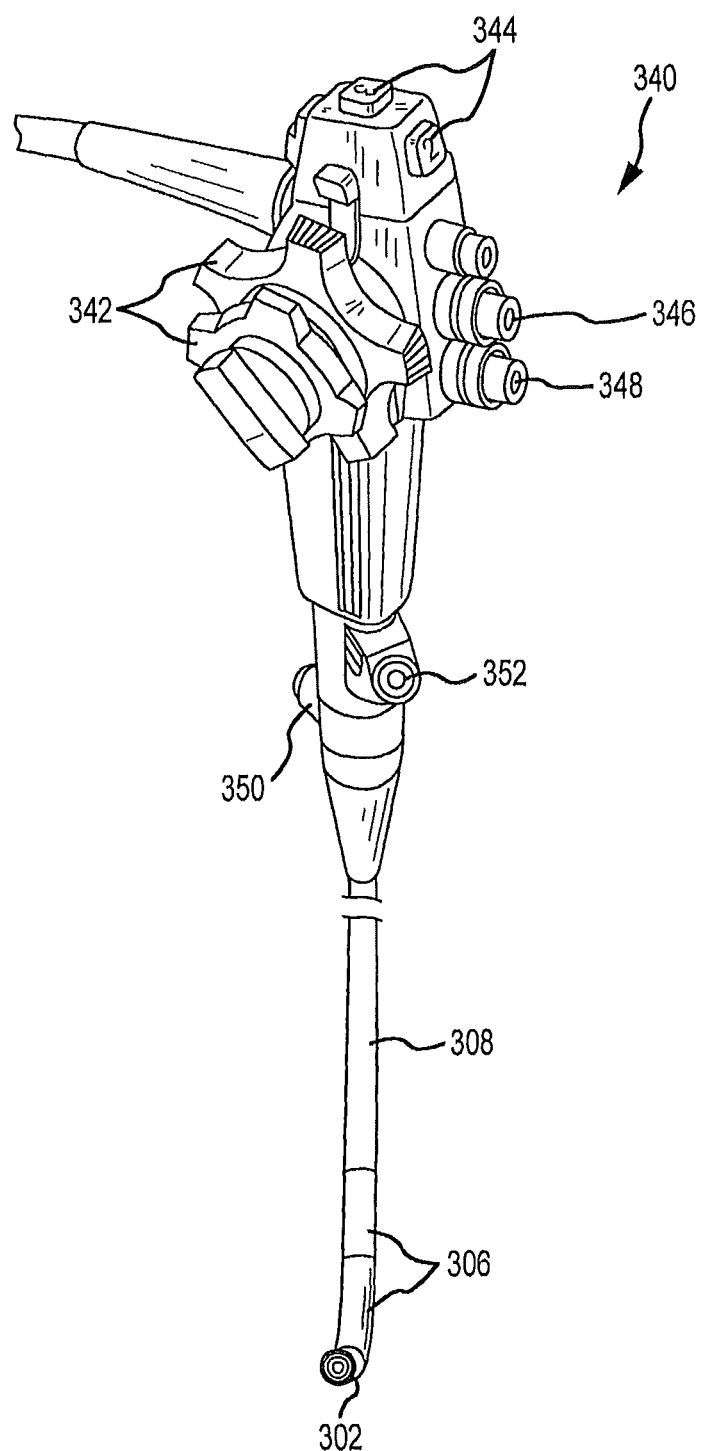
FIG. 13 is a fragmentary perspective view illustrating the endoscopic instrument connected to a conventional steering device enabling precise and accurate steering of the distal tip of the endoscopic instrument.

Referring to FIG. 13, the endoscopic device is illustrated as connected to a conventional steering assembly 340 that is used to facilitate a number of functions for the endoscopic device, to include steering of the endoscopic device and the introduction of various fluids or instruments through the endoscopic device. Accordingly, the steering assembly 340 is illustrated with conventional controls, to include, steering controls 342 which can tension or loosen the wires to effect a desired articulation of the distal end of the endoscope. For example, one of the knobs/dials can control transverse movement while the other knob/dial can control longitudinal movement. The FIG. 13 also shows other conventional controls such as frame and shutter controls 344 for the imaging device, and various ports to receive gas, fluids and/or instruments. For example, the FIG. 13 shows a suction port 346, an air port 348, an auxiliary port 350, and a biopsy port 352. The ports 350 and 352 may receive instruments for conducting the desired surgical procedure, such as forceps, electrodes, etc.

The connector assembly 300 provides a structure for anchoring steering wires and for stabilizing and supporting electrical connections between the imaging device and the image/power cable. The connector assembly facilitates a steering capability but does not enlarge the frontal profile of the imaging device since the steering wires are housed within the sheath of the endoscope and are anchored internally within the distal end of the endoscope. Accordingly, the imaging device is maintained in a very small configuration which provides great advantages in terms of reducing the invasive nature of surgical procedures, as well as providing additional options for use of the imaging device to be steered into an optimal location for imaging difficult to access locations within a body. Additionally, the location at which the steering wires are anchored, namely, at the connector assembly itself, allows for optimum control in which the distal end of the endoscopic device can be maneuvered. In summary, the connector assembly fulfills two distinct purposes, namely, providing strain relief and support to the electrical traces and electrical wires, and serving to anchor the distal ends of the steering wires. The steering capability provided is usable with any of the imaging embodiments disclosed herein, to include both wired and wireless imaging capabilities.

From the foregoing, it is apparent that an entire imaging device may be incorporated within the distal tip of an endoscope, or may have some elements of the imaging device being placed in a small remote box adjacent to the endoscope. Based upon the type of image sensor used, the profile area of the imaging device may be made small enough to be placed into an endoscope which has a very small diameter tube. Additionally, the imaging device may be placed into the channels of existing endoscopes to provide additional imaging capability without increasing the size of the endoscope. The imaging device may be powered by a standard power input connection in the form of a power cord, or a small battery may be used. In order to enhance the freedom of using the endoscope without trailing cables, the endoscope may include wireless transmission capabilities. A wireless endoscope also has advantages with respect to overall surgical efficiency in conducting procedures by minimizing requirements to drape or shield cables in the sterile field, and by providing an endoscope which has unlimited movement capabilities without having to orient or otherwise handle the endoscope to account for twisted cables, drapes, or other components which are normally associated with endoscopic devices. A wireless transmission of post-video signals from the endoscope directly to the video display can be done to provide video images. Alternatively, the imaging device can be separated into components which are located in the endoscope and in a remote control box. Pre-video signals are wirelessly transmitted to the control box, and then post-video signals are provided to the video display either through a secondary wireless transmission, or by a conventional hard wired connection.

This invention has been described in detail with reference to particular embodiments thereof, but it will be understood that various other modifications can be effected within the spirit and scope of this invention.

What is claimed is:

1. An endoscopic device including an image sensor for producing images of a surgical site, said device comprising:
   a tubular portion including a distal end, a proximal end, and a central passageway extending through said tubular portion;
   an image sensor positioned in said tubular portion for receiving images of a surgical site, said image sensor producing an image signal, and said image sensor being a CMOS image sensor;
   a connector assembly for interconnecting electrical leads of the image sensor to electrical wires of an image/power cable that transmits image signals from the image sensor through the cable to a video device, said connector assembly having a body and a plurality of transverse extensions and at least one orthogonal center member connecting the lateral extensions, a plurality of gaps formed between each of said lateral extensions, said connector assembly having a proximal end thereof with a smaller width dimension;
   a plurality of electrical traces extending though the gaps of said connector assembly for electrically interconnecting the image sensor to the electrical wires of the image/power cable;
   a strain relief cap connected to said connector assembly, said strain relief cap covering at least of portion of said electrical traces extending through said connector assembly;
   a plurality of steering wires extending through said tubular portion for steering a distal end of the endoscopic device to position the image sensor, said steering wires having distal ends connected to said strain relief cap and proximal ends extending through said tubular portion; and
   a steering assembly attached at a proximal end of said tubular portion for receiving said steering wires and said cable, said steering assembly providing a steering capability to said endoscope through manipulation of said steering wires.

2. A device as claimed in claim 1, wherein:
   said strain relief cap includes a pair of channels secured over opposite lateral sides of said proximal end of said connector assembly, and said steering wires being anchored to a facing surface of said strain relief cap.

3. A device, as claimed in claim 1, wherein:
   said plurality of steering wires include four steering wires, said steering wires arranged in a rectangular arrangement and located at corners of the rectangular arrangement.

4. A device, as claimed in claim 1, wherein:
   said image sensor has a frontal profile defined by a length and width dimension, and said strain relief cap being secured to said connector assembly such that the connector assembly and strain relief cap when connected do not extend beyond said frontal profile.

5. A device, as claimed in claim 1, wherein:
   said image/power cable are located radially interior of said steering wires.

6. A device, as claimed in claim 1, wherein:
   said connector assembly further includes a portion thereof attached to said image sensor for mounting of the image sensor to the connector.

7. A device, as claimed in claim 1, wherein:
   a capsule covers said image sensor at said distal end of said tubular portion, and said capsule has a frontal profile defined by a length and width dimension, and said strain relief cap being secured to said connector assembly such that the connector assembly and strain relief cap when connected do not extend beyond said frontal profile.

8. An endoscopic device including an image sensor for producing images of a surgical site, said device comprising:
   a tubular portion including a distal end, a proximal end, and a central passageway extending through said tubular portion;
   an image sensor positioned in said tubular portion for receiving images of a surgical site, said image sensor producing an image signal, and said image sensor being a CMOS image sensor;
   a connector assembly for interconnecting electrical leads of the image sensor to electrical wires of an image/power cable that transmits image signals from the image sensor through the cable to a video device, said connector assembly having a body;
   a plurality of electrical traces extending though the gaps of said connector assembly for electrically interconnecting the image sensor to the electrical wires of the image/power cable;
   a strain relief cap connected to said connector assembly, said strain relief cap covering at least of portion of said electrical traces extending through said connector assembly;
   a plurality of steering wires extending through said tubular portion for steering a distal end of the endoscopic device to position the image sensor, said steering wires having distal ends connected to said strain relief cap and proximal ends extending through said tubular portion; and
   a steering assembly attached at a proximal end of said tubular portion for receiving said steering wires and said cable, said steering assembly providing a steering capability to said endoscope through manipulation of said steering wires;
   said connector assembly body having a plurality of transverse extensions and at least one orthogonal center member connecting the lateral extensions, a plurality of gaps formed between each of said lateral extensions, said connector assembly having a proximal end thereof with a smaller width dimension; and
   said strain relief cap includes a pair of channels secured over opposite lateral sides of said proximal end of said connector assembly, and said steering wires being anchored to a facing surface of said strain relief cap.

* * * * *